United States Patent [19]
George et al.

[11] Patent Number: 5,861,156
[45] Date of Patent: Jan. 19, 1999

[54] METHODS OF DELIVERING AGENTS TO TARGET CELLS

[75] Inventors: Andrew J. T. George, Richmond Surrey, United Kingdom; David M. Segal, Rockville, Md.; James S. Huston, Chestnut Hill, Mass.

[73] Assignees: Creative BioMolecules, Hopkinton, Mass.; The United States of America as represented by the Department of Health and Human Services, Washington, D.C.

[21] Appl. No.: 2,324

[22] Filed: Jan. 8, 1993

[51] Int. Cl.$^6$ .................. A61K 39/395; A61K 39/40; A61K 39/42; C12P 21/08
[52] U.S. Cl. ............................... 424/135.1; 424/136.1; 424/152.1; 424/154.1; 530/387.3; 530/387.1
[58] Field of Search ..................... 424/135.1, 136.1, 424/152.1, 130.1, 154.1; 530/387.3, 387.1

[56] References Cited

U.S. PATENT DOCUMENTS

| | | | |
|---|---|---|---|
| 4,676,980 | 6/1987 | Segal et al. | 424/136.1 |
| 5,084,398 | 1/1992 | Huston et al. | 436/535 |
| 5,091,513 | 2/1992 | Huston et al. | 530/387.3 |

OTHER PUBLICATIONS

Souza et al. PNAS vol. 92 p. 959–963, 1995.
Osband et al. Immunology Today vol. 11 No. 6. p. 193 1990.
Monclonal Antibodies. (Waldmann ed.) 1988 pp. 31–49.
Schlom Molecular Foundation of Oncology ed. Samuel Broder 1991 p. 95–134.
Genes and Cancer (Hird) ed. Carney and Sikora. 1990 pp. 183–189.
Waldmann Science vol. 252 1991 p. 1657.
Harris et al. Tibteln Vol. 11 1993, p. 42.
Int J. Cancer. Sugita et al. 37 1986 p. 351–357.
Friedman, P.N., et al., "Antitumor Activity of the Single-Chain Immunotoxin BR96 sFv–PE40 Against Established Breast and Lung Tumor Xenografts," *Chemical Abstracts*, 119:437–437 Abstract No. 119:4237y (1993).
Friedman, P.N. et al., "BR96 sFv–PE40, a Potent Single-Chain Immunotoxin that Selectively Kills Carcinoma Cells, " *Chemical Abstracts*, 118:32 Abstracts No. 118:93926z (1993).
Huston, J.S., et al., "Medical Applications of Single–Chain Antibodies," *Intern. Rev. Immunol.*, 10:195–217 (1993).
Gilliland, L.K., et al., "Universal bispecific antibody for targeting tumor cells for destruction by cytotoxic T cells," *Proc. Natl. Acad. Sci. USA*, 85:7719–7723 (1988).
Segal, D.M., et al., "Bispecific Antibodies in Cancer Treatment" *Biological Therapy of Cancer* vol. 2 No. 4 pp. 1–12 (1992).
Staerz, U.D. et al., "Hybrid antibody–mediated Lysis of virus–infected cells," *Eur. J. Immunol.* 17:571–574 (1987).
Milenic, D.E., et al., "Constructions, Binding Properties, Metabolism, and Tumor Targeting of a Single–Chain Fv Derived from the Pancarcinoma Monoclonal Antibody CC49", *Cancer Research*, 51:6363–6371 (1991).

Karpovsky, B., et al., "Production of Target–Specific Effector Cells Using Hetero–Cross–Linked Aggregates Containing Anti–Target Cell and Anto–Fcγ Receptor Antibodies," *J. of Exp. Med.* 160:1686–1701 (1984).
Titus, J.A., et al., "Human T Cells Targeted with Anti–T3 Cross–Linked to Antitumor Antibody Prevent Tumor Growth in Nude Mice," *J. of Immunol.*, 138:4018–4022 (1987).
Staerz, U.D. and Bevan, M.J., "Hybrid hybridoma producing a bispecific monoclonal antilbody that can focus effector T–cell activity," *Proc. Natl. Acad. Sci. USA*, 83:1453–1457 (1986).
Yokota, T., et al., "Rapid Tumor Penetration of a Single–Chain Fv and Comparison with Other Immunoglobulin Forms," *Cancer Research*, 52:3402–3408 (1992).
Marchalonis J.J. and Galbraith, R.M, "Receptors on Lymphoid Cells: An Overview," *Meth. in Enzymol..* 150:377–389 (1987).
Segal, D.M. and Snider, D.P., "targeting and Activation of Cytotoxic Lymphocytes," *Chem. Immunol.*, 47:179–213 (1989).
Perez, P., et al., "Specific targeting of cytotoxic T Cells by antil–T3 linked to anti–target cell antibody, " *Nature*, 316:354–356 (1985).
Bosslet, K., et al., "Two–phase radioimmunotherapy using bispecific monoclonal antibodies (bs MAbs)," *Cancer Treatment Reviews* 17:355–356 (1990).
Segal, D.M., et al., "Targeting of cytotoxic cells with cross–linked antibody heteroaggregates," *Mol. Immunol.*, 23(11):1211–1214 (1986).
Snider, D.P. and Segal, D.M. "Efficiency of antigen presentation after antigen targeting to surface IgD, IgM, MCH, Fcγ RII, and B220 Molecules on Murine Splenic B Cells", *J. of Immunol.*, 143(1):59–65 (1989).
Huston, J.S., et al., "Multisite association by recombinant proteins can enhance binding selectivity," *Biophysical Journal*, 62:87–91 (1992).
Segal, D.M., et al., "Targeted cytotoxic Cells as a Novel Form of Cancer Immunotherapy," *Mol. Immunol.*, 25(11):1099–1103 (1988).
Segal, D.M., et al., "Targeting of Cytotoxic Cells with Heterocrosslinked Antibodies," *Cancer Invest.,.* 6(1):83–92 (1988).
Caron, P.C., et al., "Engineered Humanized Dimeric Forms of IgG Are More Effective Antibodies," *J. Exp. Med.*, 176:1191–1195 (1992).

(List continued on next page.)

*Primary Examiner*—Lila Feisee
*Assistant Examiner*—Yvonne Eyler
*Attorney, Agent, or Firm*—Hamilton, Brook, Smith & Reynolds, P.C.

[57] ABSTRACT

Methods of delivering agents to target cells including methods of immunotherapy, are disclosed in which monospecific binding proteins are administered to a host and bind to target cells followed by administration of multivalent antibodies to direct the agents to the target cells.

22 Claims, 15 Drawing Sheets

OTHER PUBLICATIONS

Bosslet, K., et al., "Generation of bispecific monoclonal antibodies for two phase radioimmunotherapy," *Br. J. Cancer*, 63:681–686 (1991).

Shin, S–U., and Morrison, S.L., "Production and Properties of Chimeric Antibody Molecules," *Meth. in Enzymol.*, 178:459–476 (1989).

Snider, D.P., et al., "Enhanced Antigen Immunogenicity Induced by Bispecific Antibodies," *J. Exp. Med.*, 171:1957–1963 (1990).

Figure 3

A. U7.6 heavy chain variable region sequence

CAG GTC CAA CTG CAG CAG TCT GGA CCT GAG CTG GAG AAG CCT GGC
gln val gln leu gln gln ser gly pro glu leu glu lys pro gly GCT TCA GTG AAG ATA TCC TGC AAG GCT TCT GGT TAC TCA TTC ACT
ala ser val lys ile ser cys lys ala ser gly tyr ser phe thr GGC TAC ATC ATG AAC TGG GTA AAA CAG AAC AAT GGA AAG AGC CTT
gly tyr ile met asn trp val lys gln asn asn gly lys ser leu GAG TGG ATT GGA AAT ATT GCT CCT TAC TAT GGT GGT ACT AGC TAC
glu trp ile gly asn ile ala pro tyr tyr gly gly thr ser tyr AAC CAG AAG TTC AAG GGC AAG GCC ACA TTG ACT GTA GAC AAA TCC
asn gln lys phe lys gly lys ala thr leu thr val asp lys ser TCC AGC ACA GCC TAC ATG CAG CTA AGC AGC CTG ACA TCT GAG GAC
ser ser thr ala tyr met gln leu ser ser leu thr ser glu asp TCT GCA GTC TAT TTC TGT GCA AGA TGG GGA GGT ACT ATG ATT ACG
ser ala val tyr phe cys ala arg trp gly gly thr met ile thr GGT CTT GAC TAC TGG GGC CAA GGC ACC ACT CTC ACA GTC TCC TCA
gly leu asp tyr trp gly gln gly thr thr leu thr val ser ser B. U7.6 light chain variable region sequence GAT ATT GTC ATG ACC CAG TCT CCA GCA ATC ATG TCT GCA TCT CCA
asp ile val met thr gln ser pro ala ile met ser ala ser pro GGG GAA AAG GTC ACC ATG ACC TGC AGG GCC AGC TCA AGT GTA AGT
gly glu lys val thr met thr cys arg ala ser ser ser val ser TCC ACT TAC TTC CAC TGG TAC CAG CAG AAG TCA GGT GCC TCC CCC
ser thr tyr phe his trp tyr gln gln lys ser gly ala ser pro AAA CTC TGG ATT TAT AGC ACA TCC ACC TTG GCT TCT GGA GTC CCT
lys leu trp ile tyr ser thr ser thr leu ala ser gly val pro GCT CGC TTC AGT GGC AGT GGG TCT GGG ACC TCT TAC TCT CTC ACA
ala arg phe ser gly ser gly ser gly thr ser tyr ser leu thr ATC AGC AGT GTG GAG GCT GAA GAT GCT GCC ACT TAT TAC TGC CAG
ile ser ser val glu ala glu asp ala ala thr tyr tyr cys gln CAG TAC AGT GGT TAC CCG CTC ACG TTC GGT GCT GGG ACC AAG CTG
gln tyr ser gly tyr pro leu thr phe gly ala gly thr lys leu GAG CTG AAA CGC
glu leu lys arg

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..360

( x i ) SEQUENCE DESCRIPTION: SEQ ID NO:1:

| CAG | GTC | CAA | CTG | CAG | CAG | TCT | GGA | CCT | GAG | CTG | GAG | AAG | CCT | GGC | GCT | 48 |
| Gln | Val | Gln | Leu | Gln | Gln | Ser | Gly | Pro | Glu | Leu | Glu | Lys | Pro | Gly | Ala | |
| 1 | | | | 5 | | | | | 10 | | | | | 15 | | |

| TCA | GTG | AAG | ATA | TCC | TGC | AAG | GCT | TCT | GGT | TAC | TCA | TTC | ACT | GGC | TAC | 96 |
| Ser | Val | Lys | Ile | Ser | Cys | Lys | Ala | Ser | Gly | Tyr | Ser | Phe | Thr | Gly | Tyr | |
| | | | 20 | | | | | 25 | | | | | 30 | | | |

| ATC | ATG | AAC | TGG | GTA | AAA | CAG | AAC | AAT | GGA | AAG | AGC | CTT | GAG | TGG | ATT | 144 |
| Ile | Met | Asn | Trp | Val | Lys | Gln | Asn | Asn | Gly | Lys | Ser | Leu | Glu | Trp | Ile | |
| | | 35 | | | | | 40 | | | | | 45 | | | | |

| GGA | AAT | ATT | GCT | CCT | TAC | TAT | GGT | GGT | ACT | AGC | TAC | AAC | CAG | AAG | TTC | 192 |
| Gly | Asn | Ile | Ala | Pro | Tyr | Tyr | Gly | Gly | Thr | Ser | Tyr | Asn | Gln | Lys | Phe | |
| 50 | | | | | | 55 | | | | | 60 | | | | | |

| AAG | GGC | AAG | GCC | ACA | TTG | ACT | GTA | GAC | AAA | TCC | TCC | AGC | ACA | GCC | TAC | 240 |
| Lys | Gly | Lys | Ala | Thr | Leu | Thr | Val | Asp | Lys | Ser | Ser | Ser | Thr | Ala | Tyr | |
| 65 | | | | | 70 | | | | | 75 | | | | | 80 | |

| ATG | CAG | CTA | AGC | AGC | CTG | ACA | TCT | GAG | GAC | TCT | GCA | GTC | TAT | TTC | TGT | 288 |
| Met | Gln | Leu | Ser | Ser | Leu | Thr | Ser | Glu | Asp | Ser | Ala | Val | Tyr | Phe | Cys | |
| | | | | 85 | | | | | 90 | | | | | 95 | | |

| GCA | AGA | TGG | GGA | GGT | ACT | ATG | ATT | ACG | GGT | CTT | GAC | TAC | TGG | GGC | CAA | 336 |
| Ala | Arg | Trp | Gly | Gly | Thr | Met | Ile | Thr | Gly | Leu | Asp | Tyr | Trp | Gly | Gln | |
| | | | 100 | | | | | 105 | | | | | 110 | | | |

| GGC | ACC | ACT | CTC | ACA | GTC | TCC | TCA | | | | | | | | | 360 |
| Gly | Thr | Thr | Leu | Thr | Val | Ser | Ser | | | | | | | | | |
| | | 115 | | | | | 120 | | | | | | | | | |

( 2 ) INFORMATION FOR SEQ ID NO:2:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Gln | Val | Gln | Leu | Gln | Gln | Ser | Gly | Pro | Glu | Leu | Glu | Lys | Pro | Gly | Ala |
| 1 | | | | 5 | | | | | 10 | | | | | 15 | |

| Ser | Val | Lys | Ile | Ser | Cys | Lys | Ala | Ser | Gly | Tyr | Ser | Phe | Thr | Gly | Tyr |
| | | | 20 | | | | | 25 | | | | | 30 | | |

| Ile | Met | Asn | Trp | Val | Lys | Gln | Asn | Asn | Gly | Lys | Ser | Leu | Glu | Trp | Ile |
| | | 35 | | | | | 40 | | | | | 45 | | | |

| Gly | Asn | Ile | Ala | Pro | Tyr | Tyr | Gly | Gly | Thr | Ser | Tyr | Asn | Gln | Lys | Phe |
| 50 | | | | | | 55 | | | | | 60 | | | | |

| Lys | Gly | Lys | Ala | Thr | Leu | Thr | Val | Asp | Lys | Ser | Ser | Ser | Thr | Ala | Tyr |
| 65 | | | | | 70 | | | | | 75 | | | | | 80 |

| Met | Gln | Leu | Ser | Ser | Leu | Thr | Ser | Glu | Asp | Ser | Ala | Val | Tyr | Phe | Cys |
| | | | | 85 | | | | | 90 | | | | | 95 | |

| Ala | Arg | Trp | Gly | Gly | Thr | Met | Ile | Thr | Gly | Leu | Asp | Tyr | Trp | Gly | Gln |
| | | | 100 | | | | | 105 | | | | | 110 | | |

| Gly | Thr | Thr | Leu | Thr | Val | Ser | Ser |
| | | 115 | | | | | 120 |

( 2 ) INFORMATION FOR SEQ ID NO:3:

( i ) SEQUENCE CHARACTERISTICS:
        ( A ) LENGTH: 327 base pairs
        ( B ) TYPE: nucleic acid
        ( C ) STRANDEDNESS: double
        ( D ) TOPOLOGY: linear (i i) MOLECULE TYPE: DNA (genomic)

(i x) FEATURE:
    (A) NAME/KEY: CDS
    (B) LOCATION: 1..327

(x i) SEQUENCE DESCRIPTION: SEQ ID NO:3:

| GAT | ATT | GTC | ATG | ACC | CAG | TCT | CCA | GCA | ATC | ATG | TCT | GCA | TCT | CCA | GGG | 48 |
|---|---|---|---|---|---|---|---|---|---|---|---|---|---|---|---|---|
| Asp | Ile | Val | Met | Thr | Gln | Ser | Pro | Ala | Ile | Met | Ser | Ala | Ser | Pro | Gly | |
| 1 | | | | 5 | | | | | 10 | | | | | 15 | | |
| GAA | AAG | GTC | ACC | ATG | ACC | TGC | AGG | GCC | AGC | TCA | AGT | GTA | AGT | TCC | ACT | 96 |
| Glu | Lys | Val | Thr | Met | Thr | Cys | Arg | Ala | Ser | Ser | Ser | Val | Ser | Ser | Thr | |
| | | | 20 | | | | | 25 | | | | | 30 | | | |
| TAC | TTC | CAC | TGG | TAC | CAG | CAG | AAG | TCA | GGT | GCC | TCC | CCC | AAA | CTC | TGG | 144 |
| Tyr | Phe | His | Trp | Tyr | Gln | Gln | Lys | Ser | Gly | Ala | Ser | Pro | Lys | Leu | Trp | |
| | | 35 | | | | | 40 | | | | | 45 | | | | |
| ATT | TAT | AGC | ACA | TCC | ACC | TTG | GCT | TCT | GGA | GTC | CCT | GCT | CGC | TCC | AGT | 192 |
| Ile | Tyr | Ser | Thr | Ser | Thr | Leu | Ala | Ser | Gly | Val | Pro | Ala | Arg | Ser | Ser | |
| | 50 | | | | | 55 | | | | | 60 | | | | | |
| GGC | AGT | GGG | TCT | GGG | ACC | TCT | TAC | TCT | CTC | ACA | ATC | AGC | AGT | GTG | GAG | 240 |
| Gly | Ser | Gly | Ser | Gly | Thr | Ser | Tyr | Ser | Leu | Thr | Ile | Ser | Ser | Val | Glu | |
| 65 | | | | | 70 | | | | | 75 | | | | | 80 | |
| GCT | GAA | GAT | GCT | GCC | ACT | TAT | TAC | TGC | CAG | CAG | TAC | AGT | GGT | TAC | CCG | 288 |
| Ala | Glu | Asp | Ala | Ala | Thr | Tyr | Tyr | Cys | Gln | Gln | Tyr | Ser | Gly | Tyr | Pro | |
| | | | | 85 | | | | | 90 | | | | | 95 | | |
| CTC | ACG | TTC | GGT | GCT | GGG | ACC | AAG | CTG | GAG | CTG | AAA | CGC | | | | 327 |
| Leu | Thr | Phe | Gly | Ala | Gly | Thr | Lys | Leu | Glu | Leu | Lys | Arg | | | | |
| | | | 100 | | | | | 105 | | | | | | | | |

(2) INFORMATION FOR SEQ ID NO:4:

(i) SEQUENCE CHARACTERISTICS:
        (A) LENGTH: 109 amino acids
        (B) TYPE: amino acid
        (D) TOPOLOGY: linear (i i) MOLECULE TYPE: protein (x i) SEQUENCE DESCRIPTION: SEQ ID NO:4:

| Asp | Ile | Val | Met | Thr | Gln | Ser | Pro | Ala | Ile | Met | Ser | Ala | Ser | Pro | Gly |
|---|---|---|---|---|---|---|---|---|---|---|---|---|---|---|---|
| 1 | | | | 5 | | | | | 10 | | | | | 15 | |
| Glu | Lys | Val | Thr | Met | Thr | Cys | Arg | Ala | Ser | Ser | Ser | Val | Ser | Ser | Thr |
| | | | 20 | | | | | 25 | | | | | 30 | | |
| Tyr | Phe | His | Trp | Tyr | Gln | Gln | Lys | Ser | Gly | Ala | Ser | Pro | Lys | Leu | Trp |
| | | 35 | | | | | 40 | | | | | 45 | | | |
| Ile | Tyr | Ser | Thr | Ser | Thr | Leu | Ala | Ser | Gly | Val | Pro | Ala | Arg | Ser | Ser |
| | 50 | | | | | 55 | | | | | 60 | | | | |
| Gly | Ser | Gly | Ser | Gly | Thr | Ser | Tyr | Ser | Leu | Thr | Ile | Ser | Ser | Val | Glu |
| 65 | | | | | 70 | | | | | 75 | | | | | 80 |
| Ala | Glu | Asp | Ala | Ala | Thr | Tyr | Tyr | Cys | Gln | Gln | Tyr | Ser | Gly | Tyr | Pro |
| | | | | 85 | | | | | 90 | | | | | 95 | |
| Leu | Thr | Phe | Gly | Ala | Gly | Thr | Lys | Leu | Glu | Leu | Lys | Arg | | | |
| | | | 100 | | | | | 105 | | | | | | | |

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:5:

```
        Glu  Gln  Lys  Leu  Ile  Ser  Glu  Glu  Asp  Leu  Asn
          1              5                        10
```

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
ATATATCTAG  AGACAGATGG  GGGTGTCGTT  TT                                32
```

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
ATATAGCGGC  CGCCCTGCTC  ACTGGATGGT  GGGAA                             35
```

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
ATATAGCGGC  CGCCCAGGTC  CARCTGCAGC  AGYCT                             35
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
CAAAWTGTKC  TCACCCAGTC  T                                             21
```

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GAYATTGTGM  TGACMCAGTC  T                                             21
```

( 2 ) INFORMATION FOR SEQ ID NO:11:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
ATATAGAGCT  CCCGGGCCAT  GGGAGATATT  GTCATGACCC  AG                      42
```

( 2 ) INFORMATION FOR SEQ ID NO:12:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
ATATAGCGGC  CGCCACTCCC  ACCTCCGCCA  GAACCTCCGC  CTCCTGATCC  GCCACCTCCG   60
CGTTTGATCT  CCAGCTTGGT  CCC                                             83
```

( 2 ) INFORMATION FOR SEQ ID NO:13:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
ATATAGCGGC  CGCCCAGGTG  CAGCTKMAGG  AGTCA                               35
```

( 2 ) INFORMATION FOR SEQ ID NO:14:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
ATATATCTAG  ACTATCAGAC  AGATGGGGGT  GTCGTTTT                            38
```

( 2 ) INFORMATION FOR SEQ ID NO:15:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CATGCCATGA  CTCGCGGCCC  AGCCGGCCAT  GGCCGATTGT  CATGACCCAG  TCTCCA      56
```

( 2 ) INFORMATION FOR SEQ ID NO:16:

( i ) SEQUENCE CHARACTERISTICS:

( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GAGTCATTCT GCGGCCGCTG AGGAGACTGT GAGAGTGGT       39

( 2 ) INFORMATION FOR SEQ ID NO:17:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

CCGCCAGAAC CTCCGCCTCC TGATCCGCCA CCTCCGCGTT TCAGCTCCAG CTTGGTCCC       59

( 2 ) INFORMATION FOR SEQ ID NO:18:

( i ) SEQUENCE CHARACTERISTICS:
( A ) LENGTH: 62 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

GGCGGATCAG GAGGCGGAGG TTCTGGAGGA GGTGGGAGTC AGGTCCAACT GCAGCAGTCT       60
GG       62

( 2 ) INFORMATION FOR SEQ ID NO:19:

( i ) SEQUENCE CHARACTERISTICS:
( A ) LENGTH: 58 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CATGCCATGA CTCGCGGCCC AGCCGGCCAT GGCCGACATC AAGATGACCC AGTCTCCA       58

( 2 ) INFORMATION FOR SEQ ID NO:20:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

GAGTCATTCT GCGGCCGCGT GATGGTGATG GTGATGTGAG GAGACTGTGA GAGTGGT       57

METHODS OF DELIVERING AGENTS TO TARGET CELLS

GOVERNMENT FUNDING

Work described herein was partially supported by a National Institutes of Health grant to the Immune Targeting Section of the Experimental Immunology Branch of the National Cancer Institute.

DESCRIPTION

BACKGROUND OF THE INVENTION

Cytotoxic cells express specific receptors on their surfaces by which they distinguish altered or foreign cells from normal autologous cells. These receptors form multiple links to structures on target cell surfaces, leading to stable conjugates between cytotoxic and target cells. Each cytotoxic cell then delivers a "lethal hit" to its conjugate target cell and detaches from it, leaving a dying target cell and a cytotoxic cell which is free to locate and destroy another target. (Segal, D. M. et al., *Cancer Invest.* 6(1): 83–92 (1988); Segal, D. M. et al., *Mol. Immunol.* 25: 1099–1103 (1988)).

Recently, a method has been developed by which the natural recognition system of cytotoxic cells can be artificially manipulated, giving rise to cytotoxic cells of any desired specificity, including specificity against tumor cells (Segal, D. M., et al., U.S. Pat. No. 4,676,980; Karpovsky, B., et al., *J. Exp. Med.,* 160: 1686–1701 (1984); Perez, P., et al., *Nature,* 316: 354–356 (1985)). The method for retargeting cytotoxic cells employs crosslinked heterobispecific antibodies, in which one antibody is directed against the receptor on the cytotoxic cell which is involved in lysis, while the second antibody is directed against a target cell structure, for example, a tumor antigen. By linking the relevant receptor on the cytotoxic cell directly to the target cell, the crosslinked heterobispecific antibodies promote the formation of effector: target conjugates and signal the cytotoxic cell to deliver a lethal hit. Antibody heteroaggregates can be produced by chemical crosslinking, or by fusing two hybridoma cells. (Segal, D. M., et al., in: *Biological Therapy of Cancer Updates* Vol. 2, V. T. DeVita, S. Hellman, and S. A. Rosenberg, eds. J. B. Lippincott Co., Philadelphia pp. 1–12 (1992)).

In recent years a great deal of interest has been focused on redirecting cytotoxic cells to kill unwanted neoplastic or virally infected cells. A common way of doing this is to use a bispecific antibody with dual specificity for an antigen on the target cell and a triggering molecule on the effector cell (such as CD3 on T cells). Such bispecific antibodies are being used in a number of clinical trials to target T cells against tumor. (Segal, D. M. and Wunderlich, J. R., *Cancer Investigation* 6: 83–92 (1988)).

The concept of retargeted effector cells for treatment of pathological conditions, such as cancer, offers some advantages over conventional, non-targeted immunotherapy. However, immune selection of targeted cells over normal cells is still problematic. Increased selectivity may be accomplished by combining forms of therapy, such as radiation and/or chemotherapy in conjunction with immunotherapy. However, these supplemental therapies are often accompanied by serious side effects. Moreover, to reach the targeted cancer cells, these large crosslinked antibodies, must penetrate solid tumor tissue sufficiently to bind to the targeted tumor cell.

Additionally, host immune responses to xenoantibodies (i.e., antibodies produced in species other than the host undergoing treatment) have been observed in clinical trials. These responses could destroy the antitumor specificity of retargeted effector cells. Furthermore, clearance of unbound crosslinked antibodies of this size, as well as clearance of the antibodies following binding, is also a problem.

Finally, retargeted effector cells may lose their artificially acquired tumor receptors (the heterobispecific antibodies) by interaction with tumor cells, by effector cell division, by endocytosis, by proteolytic extracellular enzymes, or by natural shedding. Antitumor activity in the host can be maintained by repeated treatments with effector cells and targeting antibodies. However, it is expensive and time consuming to produce large quantities of heterobispecific antibodies with the specificity necessary to interact with the intended target such as cell surface tumor antigens. Thus, it would be advantageous to be able to produce large amounts of clinical grade bispecific antibodies, for use with many different tumor antigens or cell surface markers for repeated treatment.

SUMMARY OF THE INVENTION

The present invention relates to methods of delivering agents to target cells. The target cells are modified by one or more monospecific binding proteins reactive with one, or more, naturally-occurring target cell surface markers. The monospecific binding protein reactive with the cell surface marker is tagged, fused to, or labelled with a chemical moiety which is recognized by, and binds to a site on a multivalent antibody, which also binds an agent to be delivered. The agent is bound to the multivalent antibody, which in turn, is also bound to a tagged monospecific binding protein which is bound to a cell surface marker on a target cell. Thus, the agent is delivered, or directed, to the target cells.

Chemical moiety, as used herein, includes a genetically fused or otherwise coupled peptide, one or more peptides within the sequence of a mono- or bispecific binding protein, a posttranslationally or chemically modified peptide, a chemical substituent such as biotin, incorporated into the protein, or any non-natural amino acid incorporated into the binding protein. Chemical moiety also includes any protein or parts thereof, or peptide comprising an amino acid sequence that is reactive with a recognition site, including a linker connecting variable regions of a single-chain Fv (sFv) or sFv fusion protein, or an epitope of the monospecific binding protein.

Selectivity, as used herein, refers to the recognition of targeted cells, as opposed to non-targeted, or normal, cells. Specificity, as used herein, refers to the recognition of unique cell surface components, such as antigens or receptors by a binding molecule. Recognition site refers to the part of a binding molecule that is reactive with, associates with, or binds to, a chemical moiety. The recognized site may be a binding site on a protein, a continuous or discontinuous epitope of a protein, or a peptide or chemical substituent added chemically or biochemically.

The host can be a mammalian host, including humans, domestic animals (e.g., dogs, cats, horses), mice or rats.

The term monospecific binding protein is intended to encompass binding protein fragments such as Fab and F(ab)'2 fragments, Fab fusion proteins (Better, M. and Horwitz, A. H., *Meth. Enzymol.* 178: 476–496 (1989), single-chain Fv (sFv) proteins (also referred to herein as single-chain antibodies) single-chain Fv fusion proteins, chimeric antibody proteins (e.g., recombinant antibody proteins derived from transfectoma cells (Shin, S.-U. and Morrision, S. L., *Meth. Enzymol.* 178: 459–476 (1989); Love, T. W., et al., *Meth. Enzymol.* 178: 515–527 (1989)), chimeric single-chain proteins and other single-chain fusion Fv analog proteins, such as single-chain T cell receptors. The preferred monospecific binding protein is a single-chain antibody. The term monospecific binding protein is also intended to encompass mixtures of more than one monospecific binding protein reactive with naturally-occurring cell surface components (e.g., a cocktail of different types of monospecific binding proteins reactive with a number of different cell surface epitopes).

The term multivalent antibody is intended to encompass any multivalent antibody including polyclonal or monoclonal antibodies (e.g., IgG or IgM), crosslinked heterobispecific whole antibodies, (polyclonal or monoclonal) crosslinked biologically functional fragments thereof (e.g., Fab fragments) chimeric antibodies comprising proteins from more than one species, bispecific single-chain antibodies, chimeric single-chain antibody analogs and homodimeric IgG molecules. These multivalent antibody proteins can be produced by known laboratory methods.

In a preferred embodiment, the monospecific binding protein binding to the target cell surface marker is a single-chain antibody (sFv); the chemical moiety is a peptide tag (e.g., an amino acid sequence); and the multivalent antibody is a heterobispecific antibody which binds to the peptide tag of the sFv and also binds to an agent to be delivered to the target cell, such as an effector cell.

In another embodiment, the method of delivering, or directing, agents to a target cell uses a mixture, or cocktail, of monospecific binding proteins. This cocktail contains a number of different types of monospecific binding proteins, each type of binding protein being specific for a different cell surface marker, epitope, or antigen, on the target cell. Thus, because each class of target cell has its own unique cell surface component profile, the target cell can be modified with greater specificity than with monospecific binding proteins to a single surface component alone.

The present invention further relates to a method of immunotherapy in a host whereby target cells are destroyed with enhanced selectivity using target cell-directed cytotoxic agents. This method of immunotherapy involves two concepts: the specific modification of the target cell with chemical moiety-labeled monospecific binding proteins and the targeting of cytotoxic agents to the modified target cells.

The method of immunotherapy described herein, comprises administering to a host a monospecific binding protein which binds to one or more naturally-occurring cell surface markers, and thus, "modifies" the target cell. The monospecific binding protein is tagged with a chemical moiety, such as a peptide. Subsequent to the modification of the target cell, a multivalent antibody which binds to the chemical moiety-tagged target cell and also binds a cytotoxic agent, is administered to the host.

Alternatively, cytotoxic agents such as cytotoxic T-lymphocytes (CTLS) may be coated with multivalent antibodies in vitro and the retargeted (i.e., directed to the target cell for delivery) CTL's administered after the first step of target cell modification. Because the tagged-monospecific binding protein is smaller than a whole, intact heterobispecific antibody, the unbound tag clears from the circulation much faster than the larger bispecific antibody. This greatly reduces background, nonspecific binding, and serum levels of the tagged monospecific binding protein. Thus, the cytotoxic agent destroys the target cell with enhanced selectivity, based on the unique modification of the target cell by the tagged monospecific binding protein.

In another embodiment, the binding affinity between the peptide-tagged (or moiety labeled) monospecific binding protein and the multivalent antibody is altered or decreased (i.e., reduced to lower than normal binding affinity). Effective targeting with this decreased binding affinity takes advantage of multi-site contacts between CTL-bound multivalent antibodies and the modified target cell, and thus, results in more specific interaction between the agent to be delivered and the target cell. For example, the decreased binding affinity between modified target cell and multivalent antibody precludes weak single-site targeting and strongly favors binding of the cytotoxic agent to the target cell with the enhanced selectivity of multi-site interaction. The decreased binding affinity can be accomplished by mutating the amino acid sequence of the peptide tag, (or structure of the chemical moiety) or the sequence of the multivalent antibody such that the affinity of the multivalent antibody for the peptide tag is decreased.

The utility of binding proteins having two independent binding sites of different selectivity for the treatment or control of tumors, viral infected cells, bacteria and other pathogenic states has been recognized. (Segal, D. M. and Snider, D. P., *Chem. Immunol.* 47:179–213 (1989); (Segal, D. M., et al., in: *Biological Therapy of Cancer Updates* Vol. 2, V. T. DeVita, S. Hellman, and S. A. Rosenberg, eds. J. B. Lippincott Co., Philadelphia pp. 1–12 (1992)). However, conventional bispecific antibodies (e.g., cross-linked antibodies) are too large to easily penetrate solid tumors. Thus, an immunotherapy approach that uses a monospecific binding protein with a multivalent antibody has a number of advantages.

Additional benefits derive from the incorporation of standardized epitopes on antigen binding regions that are targeted to specific surface components on target cells. These separate targeting regions are advantageous because they are typically of a smaller size than the heterobispecific antibody, the binding of which will serve to localize or "fix" the antigen binding regions in situ to enhance target localization.

The monospecific binding protein has a unique ability to penetrate solid tumors and to be rapidly cleared from the circulation if not localized at a target site. Thus, these proteins are extremely suitable for tumor immunotherapy. The monospecific binding protein also shows negligible nonselective binding and unwanted deposition in organs, such as the kidney (Yakota, T., et al., *Cancer Res.* 52: 3402–3408 (1992)). Because of its small size, usually less than 52,000 mol. wt. and preferably less than 30,000 mol. wt., the monospecific binding protein is less immunogenic and thus, less likely to cause a host immune reaction during the course of therapy. Also because of its small size, the monospecific binding protein is less susceptible to proteolysis. Thus, the monospecific binding protein is reasonably a more stable reagent.

Furthermore, any monospecific binding protein can be constructed with a distinctive chemical moiety which is recognized by the multivalent antibody. Thus, a generic multivalent antibody can be constructed which binds a distinctive peptide tag at one binding site of and an agent to be delivered at the second binding site, for universal use in any number of immunotherapeutic situations. Additionally, the methods of immunotherapy described herein, can target anything that is recognized by the non-peptide multivalent binding sites. Thus, one can target a cytotoxic lymphocyte, a radioisotope, an imaging agent or a lethal drug to destroy the target cell.

The same peptide-tagged monospecific binding protein can be tested or used for different regimes or therapy without reworking the monospecific binding protein structure or production protocol. Moreover, since the peptide-tagged monospecific binding protein is not toxic by itself, the therapeutic window for a combination, two-stage immunotherapy should be far greater than would be possible for a single administration of toxic immunoconjugate. (Bosslet, P., et al., *Cancer Treat. Rev.* 17: 355–356 (1990); Bosslet, P., et al., *Br. J. Cancer,* 63: 681–686 (1991).

Furthermore, a unique advantage of this method of immunotherapy is that it allows multi-site targeting based on moiety-tagged monospecific binding protein cocktails. For example, a cocktail can comprise a mixture of sFv proteins each sFv having a standardized chemical moiety common to the mixture of sFv proteins, yet different sFv proteins can bind to distinct antigens on the tumor or other target cells. Multi-site interactions would be necessary if antibodies are chosen with low binding constants for association with the chemical moiety. Alternatively, a lower than normal binding constant can be attained by using a truncated, or otherwise, mutated peptide tag sequence. Below some threshold affinity, e.g., $K_{a,intrinsic}=10^3 M^-$, the cell-directed cytotoxic agent would be unable to effectively bind through one or even two contacts, but with higher numbers of interactions, multi-site binding can be very tight. Thus, a very stable target:effector conjugate is formed.

Furthermore, the selectivity of the cell-directed cytotoxic agent is enhanced by multi-site targeting. A major problem of cancer immunotherapy is escape of variants, or loss of surface epitopes on the cancer cells due to mutations. George, A. J. T., et al., *International Rev. Immunol.* 4: 271–310 (1989). The problem is minimized by the use of multi-site targeting immunotherapy as described herein. For example, if a tumor cell has four unique epitopes as targets, but only one epitope is targeted, and that one epitope is lost through mutation, successful treatment using a single target immunotherapy which targets the lost epitope is precluded. However, with multi-site targeting, which would target all four epitopes, if one epitope is lost, the treatment can still be successful because three remaining epitopes are available for targeting of the therapeutic agent.

BRIEF DESCRIPTION OF THE DRAWINGS

FIG. 3A is the DNA sequence (SEQ ID NO:1) of the VH region of U7.6 sFv with its predicted amino acid sequence (SEQ ID NO:2).

FIG. 3B is the DNA sequence (SEQ ID NO:3) of the VL region of U7.6 sFv with its predicted amino acid sequence (SEQ ID NO:4).

DETAILED DESCRIPTION OF THE INVENTION

The present invention relates to methods of delivering or directing, agents to target cells. The target cell is modified by one or more monospecific binding proteins reactive with one, or more, naturally-occurring target cell surface markers. The monospecific binding protein reactive with the cell surface marker is tagged, fused to, or labelled with a chemical moiety which is recognized by, and binds to a site on a multivalent antibody, which also binds an agent to be delivered. Thus, the agent is delivered, or directed, to the target cell.

Specifically, a monospecific binding protein bound to a cell surface marker is tagged, or labelled, with a chemical moiety which serves as a contact, or signal, for association with a recognition site on a multivalent antibody. This multivalent antibody also binds an agent to be delivered, or directed to, the target cell, at another binding site. Thus, the agent is delivered to the target cell through the association of the recognition site on the multivalent antibody and chemical moiety of the modified target cell.

The target cells of the present invention include any cell in a mammalian host which is undesirable and needs to be eliminated, controlled, attacked and/or destroyed functionally or otherwise. In particular, target cells can be tumor cells, bacteria-infected cells, virus-infected cells, or autoimmune cells.

The target cells have naturally-occurring cell surface components, or markers. These surface markers include specific receptors, such as the melanocyte-stimulating hormone (MSH) receptor expressed on melanoma cells, or selective antigens, such as the human cancer antigen CA125 expressed on ovarian carcinoma cells. Cell surface markers also include the major histocompatibility complex molecules (MHC I or MHC II), and virus-infected cells often express viral antigens on their surfaces. Taken together, a cell's surface components present a surface marker profile unique to that particular type of cell.

The cell's surface markers can be used to direct agents, such as imaging agents, other antibodies and cytotoxic agents, such as drugs or cytotoxic effector cells, to be delivered to the cell. Cytotoxic agents can include cytotoxic drugs and radionucleotides effective in chemical or radiation therapy. For example, a drug can be designed to bind to a cell surface receptor and block ligand binding, or an antibody can be specifically bound to a target cell via a cell surface marker, thus, flagging the target cell for cells mediating antibody-dependent cellular cytotoxicity. However, drugs and antibodies directed to naturally-occurring cell surface markers may not be totally selective for the target cell, resulting in destruction of normal as well as malignant cells.

Figure 5:
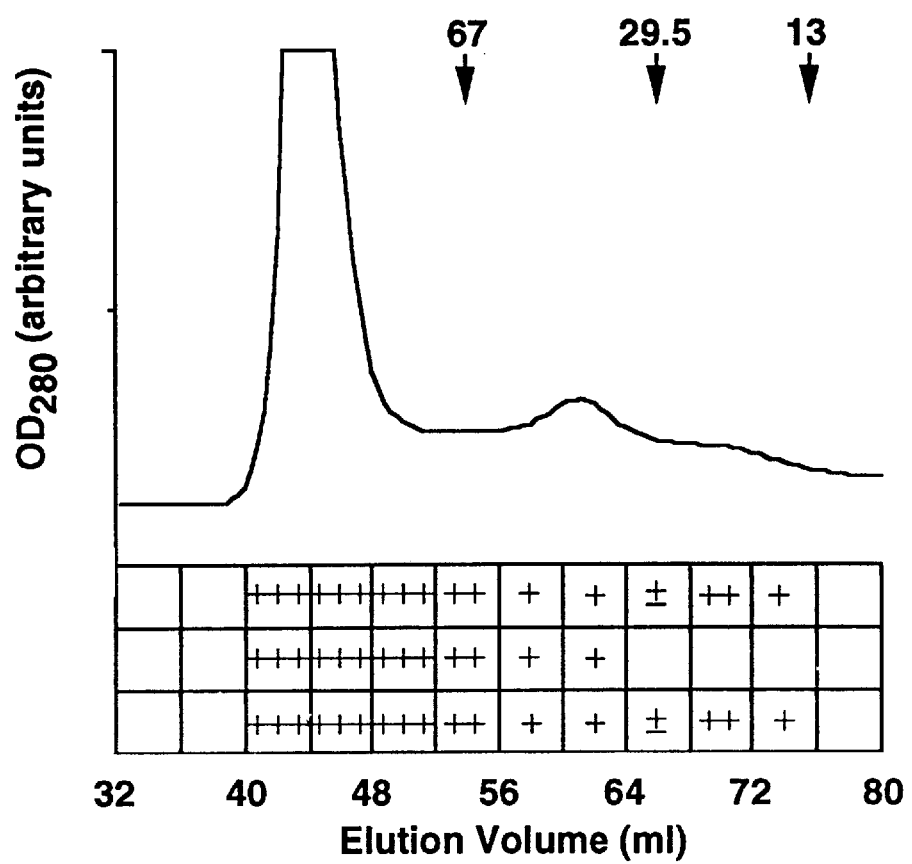
FIG. 5 is a graphic representation of the size analysis of renatured U7.6 sFv (upper profile) and dot-blot data showing specific absorption to DNP-lysine-Sepharose (lower panels).

As described herein, a target cell is modified to enhance the selective binding of target cell-directed cytotoxic agents to the target cell. A target cell is modified by one or more monospecific binding proteins reactive with (bound to) one, or more, of the naturally-occurring cell surface markers. The monospecific binding protein can be a binding protein fragment such as an Fab, Fab' or an F(ab)'2 antibody fragment, which is prepared by conventional laboratory methods. Monospecific binding proteins can also be single-chain Fv fusion proteins (sFv), single-chain antibodies, chimeric single-chain protein analogs and other single-chain fusion proteins, such as single-chain T cell receptors. In a preferred embodiment, the monospecific binding protein reactive with the target cell surface marker is a single-chain antibody. FIG. 1 is a schematic representation of a target cell modified by peptide-tagged single-chain antibodies. Bound to the peptide tag is a heterobispecific antibody, which also binds a cytotoxic T-lymphocyte.

An sFv is a genetically engineered single-chain construct of the Fv portion of an antibody molecule, or other receptor molecule of the Ig superfamily. Construction of single-chain antibody molecules are described in Huston, J. S., et al., *Proc. Natl. Acad. Sci. USA* 85:5879–5883 (1988) and Huston, J. S., et al., *Meth. Enzymol.* 203:46–88 (1991), and Huston, et al., U.S. Pat. No. 5,091,513 (the teachings of which are hereby incorporated by reference). The sFv contains two variable region domains linked together by a flexible peptide spacer. These sFv molecules contain all the information required to determine antigen specificity with none of the constant region that defines effector functions, such as interactions with the $Fc_\gamma$ receptor which binds cytotoxic effector cells. The small size of these molecules (25–30 kD) improves many of their pharmokinetic properties, increasing penetration of solid tissues, decreasing circulating half-life and reducing immunogenicity. (Yakota, T., et al., *Cancer Res.* 52:3402–3408 (1991); Milenic, D. E., et al., *Cancer Res.* 51:6363–6371 (1991)).

The single-chain antibody bound to the cell surface marker is tagged, or labelled, with a chemical moiety which serves as a contact, or signal, for association with a recognition site on a multivalent antibody and, thus, directs the multivalent antibody to bind to the target cell. In a preferred embodiment, the chemical moiety is a peptide tag comprising a short amino acid sequence, such as the 11 amino acid residue myc-tag peptide sequence EQKLISEEDLN (SEQ ID NO: 5) on a single-chain Fv protein.

Single-chain Fv proteins have been produced by eukaryotic and prokaryotic cells, and in cell free lysates. Prokaryotic expression systems offer many advantages in terms of ease of manipulation, high yields and reduced cost. However the majority of bacterial expression systems produce the recombinant proteins in insoluble inclusion bodies, necessitating complicated refolding protocols to obtain active protein. An alternative approach is to direct the protein to the periplasmic space of Gram negative bacteria, where a number of bacterial proteins can aid in the folding and oxidation of the newly synthesized protein. Such periplasmic expression systems have been used for the production of sFv proteins. (Glockshuber, et al., *Biochemistry* 29: 1362–1367 (1990)).

In some cases, the sFv proteins are isolated from the periplasmic material, while in others soluble material can be found in the growth medium, presumably due to release of the sFv from the periplasm following breakdown of the bacterial outer cell wall.

Examples 1 and 2 below, describe in detail the production of two peptide-tagged sFv proteins in the bacterial periplasm, one directed against the hapten dinitrophenol (DNP) and the other against the transferrin receptor. Using the anti-DNP sFv as a model system, additional single-chain fusion proteins with specificity for other cell surface components can be constructed. Also, as described in Example 1, these sFv proteins can be purified in an active form, without the need for large amounts of antigen for affinity purification. Examples 3 and 4 below, demonstrate that the sFv binds specifically to target cells and, when linked to an anti-CD3 antibody, are useful to redirect cytotoxic T cells to kill target cells.

A peptide tagged sFv, U7.6 sFv, specific for the hapten DNP, was constructed as described in detail in Example 1. A schematic representation of the PCR and cloning steps is presented in FIG. 2. Briefly, the V regions of the anti-DNP antibody U7.6 were amplified by PCR and originally cloned as an sFv. Sequence analysis of the V regions showed that the VL and VH domains belonged to the VKVI and VHII region families, respectively. FIG. 3A depicts the DNA sequence of the VH domain (SEQ ID NO:1), with its deduced amino acid sequence (SEQ ID NO:2) and FIG. 3B depicts the DNA sequence of the VL domain (SEQ ID NO:3) and its deduced amino acid sequence (SEQ ID NO:4). The primers that were originally used to amplify the V regions from the cDNA were designed to anneal to V regions from the VK IV or VI and the VH I and II families. Primers designed for other V region families did not amplify U7.6 cDNA (with the exception of a primer based on the VK Vb family which can amplify an aberrantly rearranged kappa chain produced by the MOPC 21 derived fusion partner used to produce the hybridoma).

In order to test the possibility of using gene splicing by overlap extension techniques to construct a peptide-tagged sFv, the construct was remade prior to cloning into the expression vector, pHEN 1. This method allows for a complete sFv to be rapidly constructed by two sequential rounds of polymerase chain reaction (PCR) amplification (FIG. 2, step 1), followed by direct cloning into the expression vector (FIG. 2, step 2). This method has an additional advantage in that it is not necessary to introduce any restriction sites between the two V region domains. The new U7.6 sFv construct was cloned into pHEN 1 in between the PelB leader sequence and a peptide tag.

For production of sFv, bacteria harboring pHEN 1 U7.6 were grown and induced with IPTG. Some active sFv (100–500 ug/liter) could be isolated directly from the culture supernatant by adsorption to DNP Sepharose beads, and elution with hapten (FIG. 4, lane 5). However, most of the sFv material was found associated with the bacteria in an insoluble form. To increase the yield of sFv the bacteria were lysed, the protein solubilized, and then allowed to renature by dialyzing against a buffer (FIG. 4, lane 3). The sFv antibody was then affinity purified (FIG. 4, lane 4). This procedure, which relies on the bacteria to form disulfide bonds in the periplasmic space, reproducibly gave high yields of sFv. In one typical experiment, a total of 4.5 mg of active sFv per liter of culture was obtained.

The DNP-binding sFv was isolated by affinity and size-exclusion chromatography, as described in Example 1. In order to determine the activity of the various fractions collected from the column, aliquots were incubated with DNP beads in the presence or absence of free DNP hapten, also as described in Example 1. The beads were then removed by centrifugation and the supernatants tested for the presence of sFv by dot blotting with the anti-peptide antibody. As shown in FIG. 5, the DNP Sepharose beads selectively removed the monomeric protein (lane B). This removal was blocked by 1 mM DNP hapten (lane C) showing that it was specific. As shown in FIG. 5, the majority of active and adsorbable U7.6 sFv resides in the monomeric peak and most, if not all, of the monomeric protein is active. Thus, size exclusion chromatography provides a relatively simple method of separating active from inactive sFv.

Figure 6:
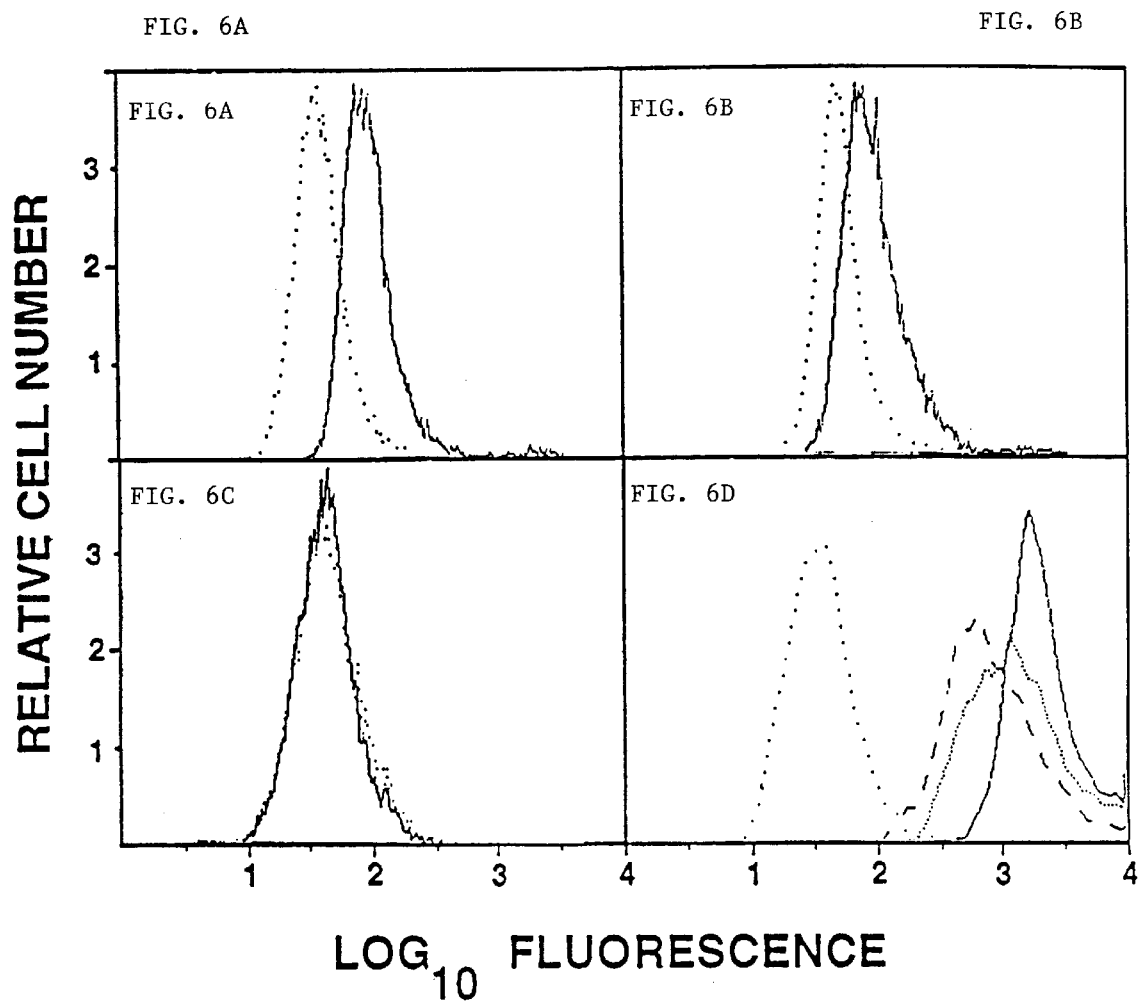
FIGS. 6A–D depict the results of binding of U7.6 sFv to TNP modified cells measured by fluorescent activated cell sorting (FACS).
Figure 7:
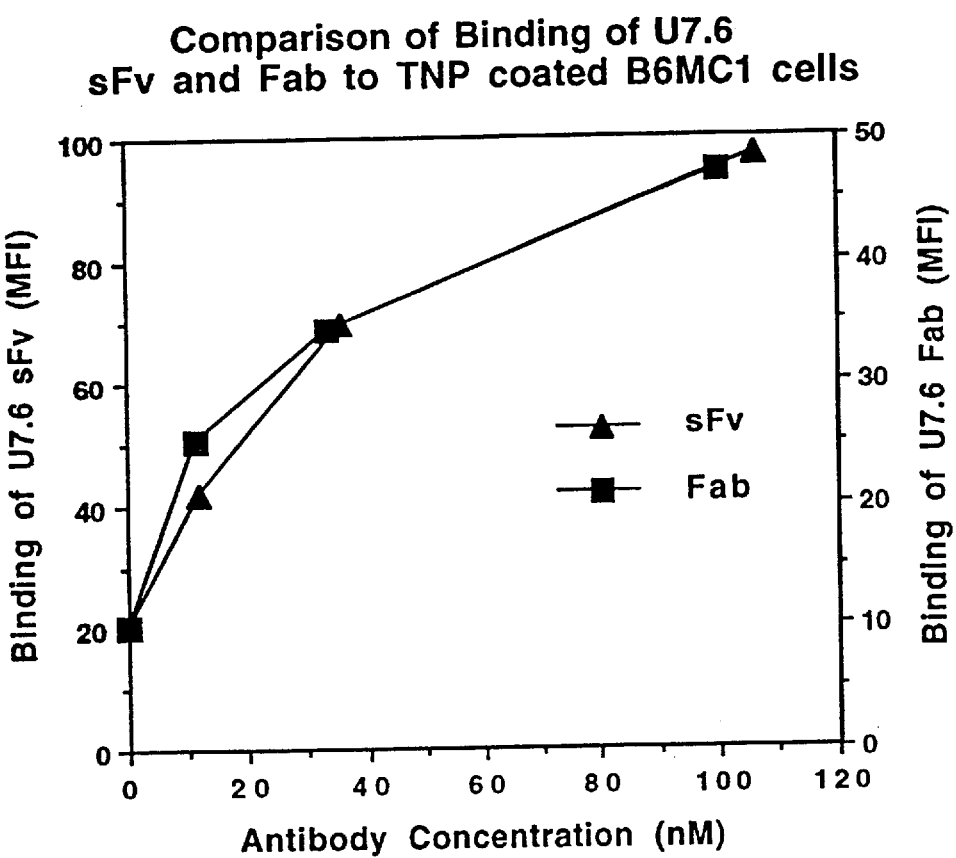
FIG. 7 shows the results of the relative binding of U7.6 sFv and Fab to TNP coated B6MC1 cells.

The ability of the U7.6 sFv to bind to cell surfaces was tested by FACS analysis, as described in Example 3, using FITC labelled Mycl 9E10.2 to detect the sFv. As is shown in FIG. 6, the U7.6 sFv binds to TNP coated B6MC1 cells, but not to B6MC1 cells alone. In addition, both U7.6 sFv and a Fab derived from U7.6 IgG bound to TNP-B6MC1 cells at similar concentrations, as shown in FIG. 7.

Figure 8:
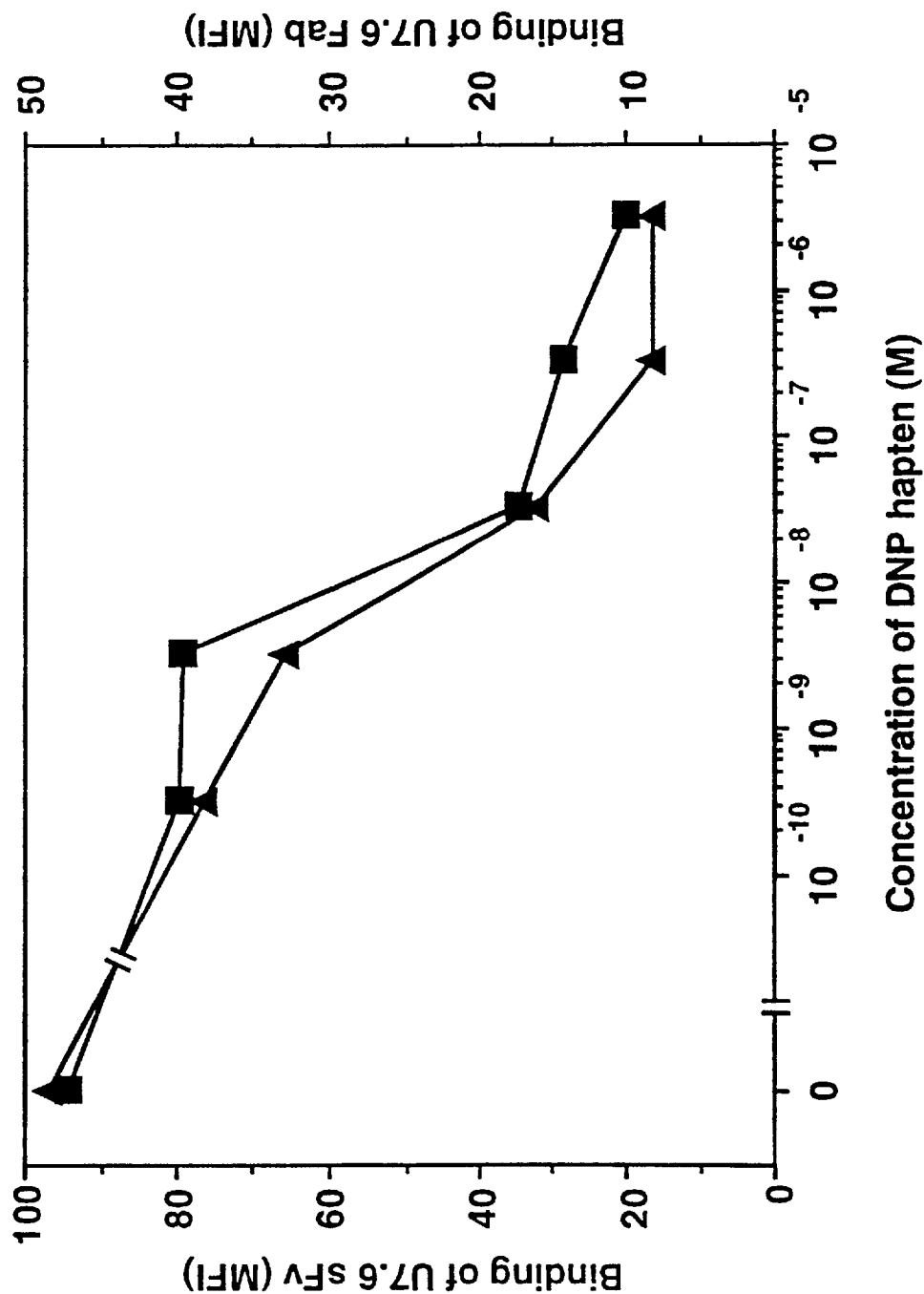
FIG. 8 shows the results of inhibition of U7.6 Fab and U7.6 sFv binding to TNP modified cells by free DNP hapten.

In order to compare the relative binding efficiencies of U7.6 sFv and U7.6 Fab, the ability of DNP hapten to inhibit the binding of the two molecules was compared. As shown in FIG. 8, the binding of both the Fab and sFv were inhibited by DNP hapten to a comparable extent, with the 50% inhibition point occurring at around $10^{-8}$M hapten.

Figure 9:
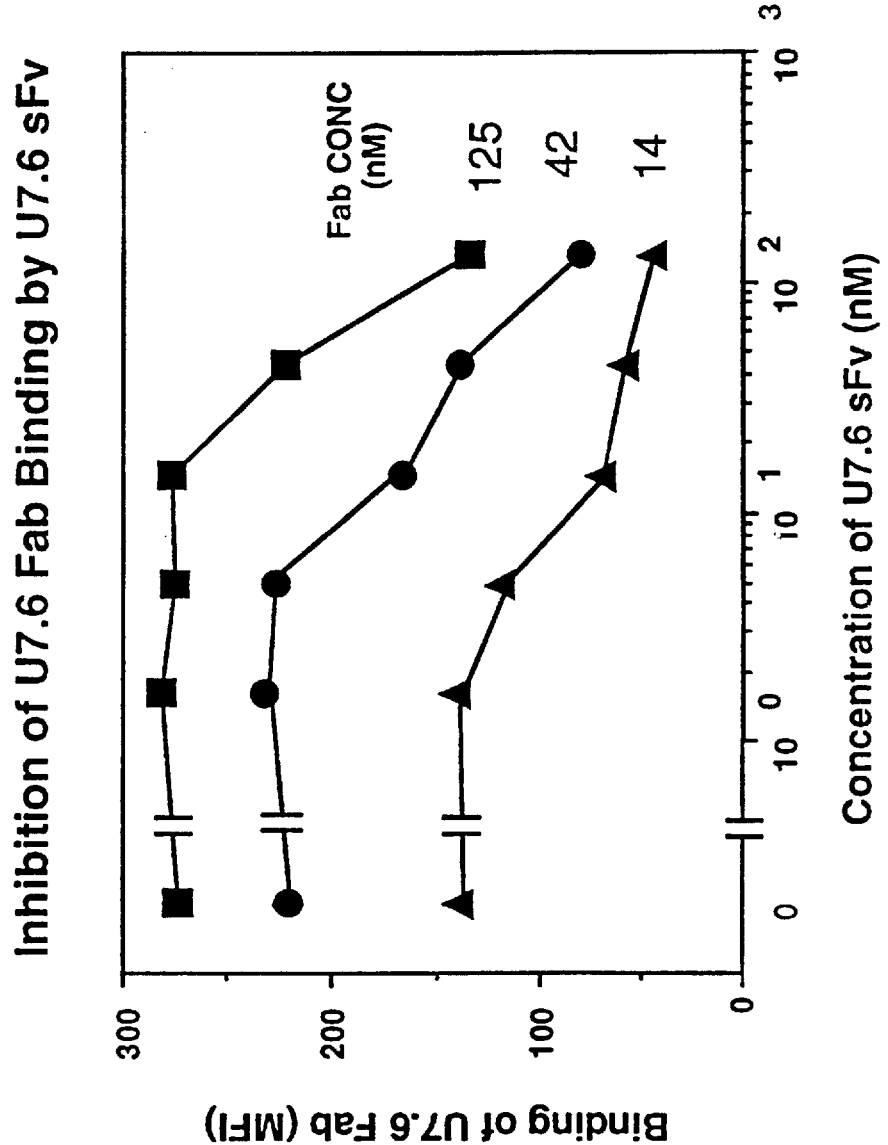
FIG. 9 shows the results of inhibition of U7.6 Fab binding to TNP modified cells by U7.6 sFv.

The binding of the U7.6 could be inhibited by the presence of U7.6 sFv (FIG. 9). When the concentrations of the two species were equimolar the binding of the U7.6 Fab was approximately half maximal, suggesting that the sFv and Fab have similar affinities for the TNP on the cell surface.

Figure 10:
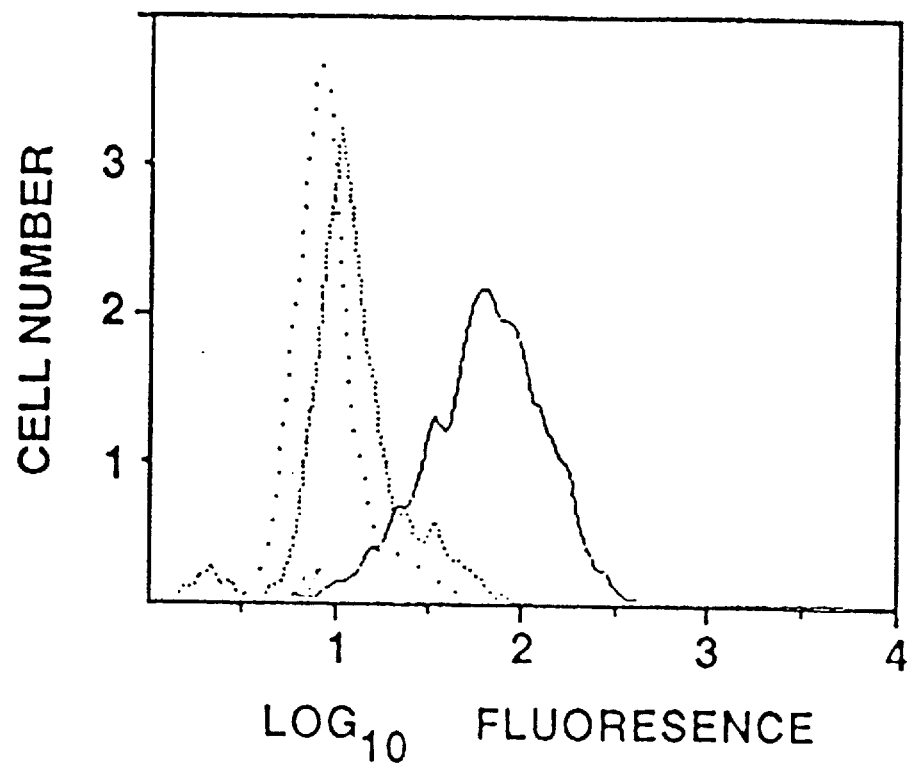
FIG. 10 shows the results of binding of OKT9 sFv to K562 cells.

In order to demonstrate that the method of production of sFv is more widely applicable, a construct was made in pHEN 1 that contained an sFv version of the OKT9 antibody, as described in Example 2. This antibody reacts with the human transferrin receptor. In addition to the VL and VH domains, joined by the same ((Gly)4Ser)3 linker used in U7.6 sFv, a hexahistidine sequence was inserted between the VH domain and the peptide tag, to allow purification by metal affinity chromatography. The OKT9 sFv was induced and solubilized in guanidine as with the U7.6 sFv, and the sFv adsorbed on $Ni^{2+}$-NTA beads followed by elution with imidazole. The purified material was then refolded by dialysis and fractionated on a Superdex 75 column. Fractions corresponding to the monomeric peak were collected and tested by FACS analysis for binding to K562 cells. As shown in FIG. 10, OKT9 sFv bound strongly to K562 cells, which express high levels of the transferrin receptor, and this binding could be inhibited by OKT9 IgG. These results were confirmed by FACS analysis of murine L cells transfected with the gene for human transferrin receptor. Unlike the U7.6 sFv, no OKT9 sFv could be detected in the culture medium following induction.

The present invention also relates to a method of immunotherapy in a host whereby target cells are destroyed with enhanced selectivity using target cell-directed cytotoxic agents. This method of immunotherapy involves two concepts: the specific modification of the target cell with chemical-moiety tagged monospecific binding protein and the targeting of cytotoxic agents to the modified target cell with enhanced selectivity.

The method of immunotherapy as described herein, comprises administering to a host a monospecific binding protein which binds to one or more naturally-occurring cell surface markers, and thus, modifies the target cell. Subsequent to the modification of the target cell, a multivalent antibody which binds to the modified target cell and to a cytotoxic agent, is administered to the host. Alternatively, the agent can be complexed with the multivalent antibody prior to host administration. Thus, the cytotoxic agent is delivered to the target cell and destroys the target cell with enhanced selectivity.

In a preferred embodiment, this method of immunotargeting uses a combination of single-chain antibodies and heterocrosslinked bispecific antibodies, wherein the target cell is modified by one or more types of single-chain antibodies which are specific for one or more cell surface markers. These single-chain antibodies are tagged with a peptide tag or chemical moiety which is recognized by a heterobispecific antibody, which also binds a cytotoxic agent. Thus, the cytotoxic agents are delivered to the target cell by heterobispecific antibodies that bind to the peptide-tagged (or chemical-moiety-tagged) single-chain antibody in a selective manner.

In other embodiments, the multivalent antibody is a Fab, Fab', or bispecific sFv. The multivalent antibody can also be a heterobispecific (Fab')$_2$ fragment, or a homodimeric (IgG)$_2$ molecule (Caron, P. C., et al., *J. Exp. Med.* 176:1191–1195 (1992)) or an IgM antibody.

Conversely, the target cell can be modified with a bispecific binding protein, such as a bispecific sFv, or a chimeric single-chain protein analog, and a multivalent antibody can be modified with a chemical moiety. Thus, the cytotoxic agent is directed to bind to the target cell through the association of the recognition site on the bispecific binding protein modifying target cell and the chemical moiety of the multivalent antibody binding the cytotoxic agent.

For example, the target cell can be modified with a chimeric single-chain protein analog (U.S. patent application Ser. No. 07/881,109, the teachings of which are hereby incorporated by reference). The chimeric protein analog can have one binding site which recognizes the naturally-occurring cell surface markers on the target cell and a second binding site which recognizes a chemical moiety associated with a second multivalent antibody, such as a heterobispecific antibody, which binds a cytotoxic lymphocyte. Thus, the cytotoxic lymphocyte is delivered to the target cell.

Alternatively, the chemical moiety tag of the monospecific binding protein can be biotin, which is reactive with a streptavidin tagged anti-CD3 antibody, which also binds a cytotoxic lymphocyte. Thus, the CTL is delivered to the target cell by the biotin-streptavidin association.

The complete antigen binding site may be obtained by recombinant methods from monoclonal antibodies or combinatorial libraries, and may correspond to the two-chain 50 kD Fab or related Fab' fragments, the two-chain 25 kD Fv fragment, or the 26–27 kD single-chain Fv. In some cases the two-chain fragments (e.g., Fab fragment) may be isolated by enzymatic digestion of a monoclonal or polyclonal antibody preparation, but the single-chain Fv (sFv) is not present in nature and can only be made through techniques of protein engineering. All of these species are smaller and far more rapid in biodistribution than IgG monomers or dimers, with typical half-lives of clearance of several days for IgG. Pharmacokinetic properties vary in relation to molecular size, such that half-lives of distribution for these monovalent binding proteins may cover a range of minutes to several hours for an Fab and to less than one hour for a single-chain Fv. Furthermore, vastly improved tumor penetration has been shown for a single-chain Fv compared to penetration of the corresponding whole IgG. (Yakota, T. et al., *Cancer Res.* 52: 3402–3408 (1992).

Thus, as described herein, this method of immunotherapy takes advantage of binding proteins of reduced size for primary targeting to the target cell, e.g., to malignant cells within a solid tumor. Fused, or conjugated, or intrinsic to these binding proteins are secondary targets (e.g., a peptide sequence or other chemical moiety) such that the secondary targets, or tags are recognized by a multivalent antibody (e.g., a heterobispecific antibody). The multivalent antibody also specifically recognizes, and tightly binds to epitopes of a cytotoxic agent or part thereof, or to cell surface markers of particular cells such as cytotoxic lymphocytes.

In one embodiment, the cytotoxic agent is an effector cell, such as a cytotoxic T-lymphocyte (CTL) which binds to the multivalent antibody. This binding can occur through "lysis promoting" receptors found on the surface of the CTL, such as the CD3 receptor. (Segal, D. M., et al., *Mol. Immunol.* 25:1099–1103 (1988)). Alternatively, surface markers for effector cells can include CD16, CD32, CD44 and other effector cell surface markers suitable for targeting. Thus, a stable conjugate is formed between the target cell and the CTL and signals are transduced which cause the CTL to deliver a "lethal hit" to the bound target cell. By linking the CTL directly to the tagged target cell, the multivalent antibody promotes the formation of effector:target conjugates and directs, or signals the CTL to deliver a lethal hit.

To demonstrate that a monospecific binding protein is capable of mediating targeted cytotoxicity, a heteroconjugate between OKT3 (anti-CD3) and Mycl 9E10.2 (anti-tag peptide), in combination with U7.6 sFv, was used to target cytotoxic T cells against TNP coated B6MC1 target cells. As described in detail in Example 4, and shown in FIG. 11, this combination of immunomolecules directed T cells to lyse TNP modified B6MC1 cells. Neither sFv, nor heteroconjugate, by themselves could direct lysis. Also as described in Example 4, the targeting could be inhibited by free hapten. B6MC1 cells that were not coated with TNP were not lysed. The lysis directed by anti-DNP U7.6 sFv-tag and anti-tag peptide×anti-CD3 bispecific antibody was comparable, though slightly lower, than that seen by a direct anti-DNP×anti-CD3 heteroconjugate. For lysis to occur, the combination U7.6 sFv-tag and heterobispecific antibody on the target cell and CD3 epitope on the cytotoxic cell had to be bridged by the tag-peptide:anti-tag antibody interaction.

Figure 12:
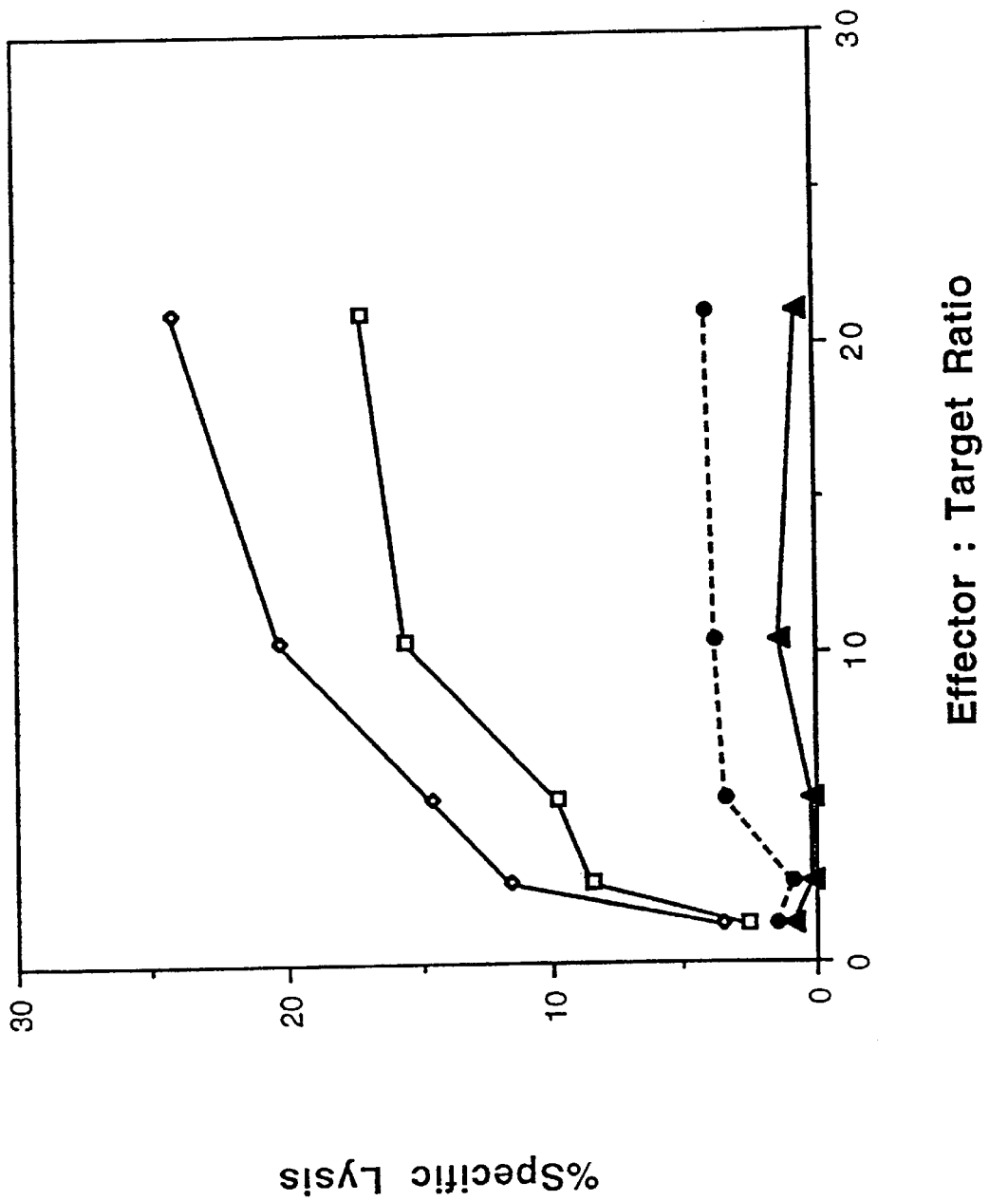
FIG. 12 shows the results of lysing TNP-TFR transfected L cells by activated human T cells.

The ability of sFv to participate in such redirected lysis was confirmed with OKT9 sFv as shown in FIG. 12. In combination with the anti-peptide×anti-CD3 heteroconjugate OKT9 sFv was capable of directing the lysis of both murine L cell transfected with the human transferrin receptor and HUT 102 cells, though not the B6MC1 cells which do not express human transferrin receptor. Again both the sFv and the heteroconjugate had to be present to elicit cytotoxicity, and the lysis was also seen with U7.6 sFv when the targets were TNP modified.

The method of immunotherapy described herein, can selectively deliver any agent that is recognized by the non-tag binding sites of the bispecific. Thus, one can direct polymeric gadolinium for MRI imaging, radioisotope complexes, or encapsulated drugs to the targeted cell.

In one embodiment of the immunotherapy described herein, the target cell can be modified by multi-site binding of peptide-tagged monospecific binding proteins. For example, a mixture, or cocktail, of single-chain antibodies can be administered to the host. This cocktail contains a number of different single-chain antibodies, each of which is specific for a different cell surface marker, or epitope, on the target cell. Thus, because each class of target cells has their own unique epitope profile, the target cell can be flagged with peptide-tagged sFv with greater specificity than with antibody to a single epitope alone.

Besides the enhanced specificity, multi-site targeting based on monospecific binding protein cocktails can enhance the selective binding of the multivalent antibody to the targeted cell even more than with single site binding. This method is analogous to the selective removal of immune complexes from blood using truncated binding proteins on insoluble matrices. (Huston, J. S., *Biophysical J.* 62:87–91 (1992); U.S. Pat. No. 5,084,398, the teachings of which are hereby incorporated by reference).

A common goal of protein engineering is to enhance recombinant binding to a cell or another protein. A typical strategy involves modifying individual protein binding sites to increase their affinity for target molecules. However, simply increasing binding affinity does not always increase specificity of binding. Significantly enhanced binding selectivity can arise from multi-site binding interactions of low individual affinity.

Figure 13:
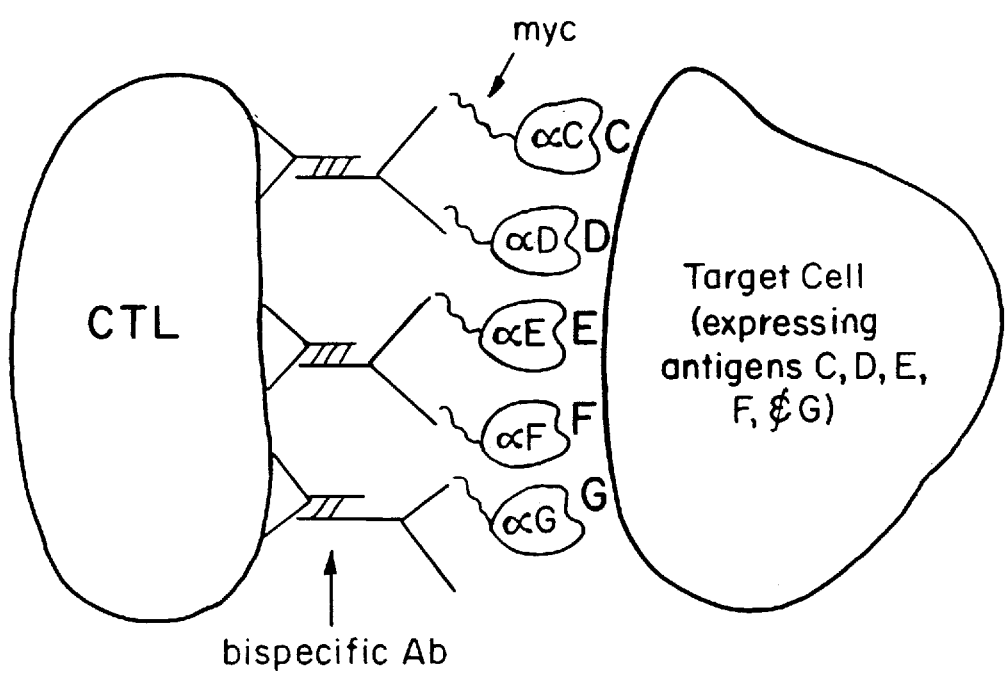
FIG. 13 is a schematic representation of multi-site binding of cytotoxic T-lymphocytes to target cells modified with multiple single-chain Fv fusion proteins.

Multivalent antibodies can be chosen with low binding constants (i.e., low affinity) for binding to the peptide sequence (or chemical moiety) tag. Alternatively, a lower binding constant can be achieved by using truncated, or altered peptide sequences (or analogs of the chemical moiety). Thus, the affinity of the bispecific antibody, or other binding protein, for the peptide tag is decreased. By making single-site contacts of such low affinity that no one-to-one complexes can form under experimental or clinical conditions, this decreased binding affinity strongly favors multi-site contacts between multivalent antibodies and the modified target cell, and thus, results in a strong interaction of enhanced specificity between (i.e., association or complexation of) cytotoxic agent to the target cell. As shown in FIG. 13, a mixture of peptide-tagged single-chain antibodies target the cytotoxic lymphocytes to distinct epitopes (C, D, E, F and G) on the target cell through multi-site interactions between the chemical moiety (tag peptide) and recognition site (part of a heterobispecific antibody that binds tag peptide). Lowering the intrinsic association constant between anti-tag binding sites and tag peptide ultimately favors multi-site binding for the mediation of targeted cytotoxicity. This multisite interaction also facilitates complex formation between the multivalent antibody and the target cell. Thus, decreasing the binding affinity of a multivalent antibody for the chemical moiety favors multisite contacts as the basis for complex formation between the multivalent antibody and target cell.

For example, at some threshold, such as below $K_{a,intrinsic}=10^3$, the targeted cytotoxic agent (e.g., a CTL) would be unable to productively bind through one, or even two, contacts under the conditions of protein concentration and target cell level present in vivo in a host. However, with multi-site interactions, binding can be very tight. Such multi-site contacts are achieved with an appropriate cocktail of monospecific binding proteins that bind to antigen at sufficient density of localization to allow multiple contacts. Enhanced selectivity may be derived from two effects. First, the effect of binding by a tagged monospecific binding protein cocktail of multiple, distinct antigens on the target cell. This effect results from the particular profile of multiple epitopes on the target cell which defines the target cell more specifically than does a single epitope, which could be present on other non-target cells. Multi-site interactions as the basis of complex formation for effective targeting of cytotoxic agents thus takes advantage of the target cell's antigen profile. Second, the effect of the surface density of a given antigen on the target cell can enhance specificity of binding, even for a single epitope. Thus, for example, a cell type with very low surface expression of a given antigen could be distinguished from a malignant cell with very high surface expression of the same antigen, since multivalent binding would very strongly favor interaction with the high-antigen-density malignant cell.

In recent years a great deal of interest has focused on redirecting cytotoxic cells to kill unwanted neoplastic or virally infected cells. A common way of doing this is to use a bispecific antibody with dual specificity for an antigen on the target cell and a triggering molecule on the effector cell (such as CD3 on T cells).

The method of immunotherapy described herein has a number of advantages over other forms of immunotherapy. First, it can be used to rapidly identify monospecific binding proteins, such as sFv proteins, that may be useful in the design and construction of recombinant bispecific antibodies. The use of a peptide tag, together with universal bispecific antibody capable of directing cytotoxic agents to destroy the sFv coated target cells, allows one to screen sFv for those with the best targeting capabilities.

Second, in a number of clinical settings, an indirect approach to targeting effector cells is advantageous. It allows use of a single sFv or a cocktail of sFvs directed against a range of epitopes on target cells, together with just one universal bispecific antibody, to enhance the affinity and specificity of the target-effector cell complex.

Furthermore, if one uses a monovalent binding protein, such an Fab or sFv fusion protein tagged with a chemical moiety, the fusion protein could be followed at an appropriate interval with the heterobispecific or tetravalent $(IgG)_2$ dimer antibody that recognizes the tagged binding proteins and crosslinks two or more binding proteins together at the cell surface. This effectively enhances target localization and improves final tumor targetability.

Finally, if the surface component of a target cell, which would be recognized by a bispecific antibody, is shed or secreted, then it may bind to effector cells coated with bispecific antibody at sites distant from the tumor, inappropriately triggering the cells to release toxic factors. This may be circumvented in the method of immunotherapy described herein, as it is possible to administer a monospecific binding protein against the cell surface component on the target cell first, and then allow any soluble antigen-binding protein complexes present to clear prior to administering the universal bispecific antibody. This would ensure that the effector cells would be directed only against target cell surface bound monospecific binding protein and, thus, deliver the effector cell to the target cell with enhanced selectivity.

The invention will be further and more specifically illustrated by the following Examples.

EXAMPLES

Example 1

Construction of the Peptide-Tagged Single-chain Fusion Protein U7.6 sFv

Cell Lines and Vectors

The following *E. coli* strains and vectors were used: XL1 blue (Stratagene, La Jolla, Calif.), TG1 and HB2151 (a gift of Dr. G. Winter, LMB, Cambridge, UK); pBluescript (Stratagene) and pHEN1 (a gift of Dr. G. Winter).

Oligonucleotides

Oligonucleotides used in this study were made on an automatic DNA synthesizer (Applied Biosystems, Foster City, Calif.), and using 'Oligonucleotide Purification Cartridges' (Applied Biosystems). The sequence of oligonucleotides used in polymerase chain reactions (PCR) are given in the Table (SEQ ID NOS:6–20).

TABLE

| Oligonucleotide Primers Used in This Study | |
|---|---|
| CH Xba | ATATATCTAGAGACAGATGGGGGTGTCGTTTT |
| CkN1 | ATATAGCGGCCGCCCTGCTCACTGGATGGTGGGAA |
| VhN1-II | ATATAGCGGCCGCCCAGGTCCA(GA)CTGCAGCAG(TC)CT |
| VkL-IV/VI | CAAA(AT)TGT(TG)CTCACCCAGTCT |
| VkL-Vb | GA(CT)ATTGTG(AC)TGAC(AC)CAGTCT |
| Vk5'exp | ATATAGAGCTCCCGGGCCATGGGAGATATTGTCATGACCCAG |
| Vk3'AL2 | ATATAGCGGCCGCCACTCCCACCTCCGCCAGAAC—<br>CTCCGCCTCCTGATCCGCCACCTCCGCGTTTG—<br>ATCTCCAGCTTGGTCCC |
| Vh Not | ATATAGCGGCCGCCCAGGTGCAGCT(GT)(AC)AGGAGTCA |
| CH1 XbaS | ATATATCTAGACTATCAGACAGATGGGGGTGTCGTTTT |
| U7.6 L5'<br>Sfi | CATGCCATGACTCGCGGCCCAGCCGGCCATGGCCGATTGTCATGACCC<br>AGTCTCCA |
| U7.6 H3'<br>Not | GAGTCATTCTGCGGCCGCTGAGGAGACTGTGAGAGTGGT |

TABLE-continued

Oligonucleotide Primers Used in This Study

| | |
|---|---|
| U7.6 L3' link | CCGCCAGAACCTCCGCCTCCTGATCCGCCACCTCCGC—GTTTCAGCTCCAGCTTGGTCCC |
| U7.6 H5' link | GGCGGATCAGGAGGCGGAGGTTCTGGAGGAGGTGGGAGTCAGGTCCAACTGCAGCAGTCTGG |
| OKT9 5' SFI | CATGCCATGACTCGCGGCCCAGCCGGCCATGGCCGACATCAAGATGACCCAGTCTCCA |
| OKT9 3' his Not | GAGTCATTCTGCGGCCGCGTGATGGTGATGGTGATGTGAGGAGACTGTGAGAGTGGT |

PCR Amplification of V Regions and Construction of U7.6 sFv mRNA from U7.6, a murine hybridoma secreting an IgG anti-dinitrophenol (DNP) antibody (a gift of Dr. Z. Eschar, Weizmann Institute, Rehovot, Israel) was prepared from the cells using a Fast Track mRNA isolation kit (InVitrogen, San Diego, Calif.). CDNA was prepared from the mRNA using MoMuLV reverse transcriptase (BRL/Life Technologies, Gaithersburg, Md.) and the CH1-Xba and CKN1 primers for the heavy and light chains, respectively. Primers were designed and used to amplify the V region domains for cloning into pBluescript consisting of VK5' exp and VK3'AL2 (VL domain) and VH Not and CH Xbas (VH domain) defined in Table 1. The VK'AL2 contains the sequence encoding the ((Gly)4Ser)3 peptide linker. The V region domains were amplified by 25 cycles of PCR (1 min 95° C., 1 min 50° C., 1 min 72° C.) using the appropriate primers and the GeneAmp kit (Perkin Elmer Cetus, Norwalk, Conn.). The resulting DNA was phenol and chloroform extracted and ethanol precipitated, cut with the appropriate restriction enzymes, electrophoresed through 2% low melt agarose gel (NuSieve, FMC Bioproducts, Rockland, Me.) and purified with Geneclean (Bio 101, La Jolla, Calif.).

The VL domain was first ligated into pBluescript at the SacI and NotI sites and the VH domain was subsequently inserted at NotI and XbaI sites. The insert from the resulting plasmid (pBluescript U7.6) was then sequenced using the Sequenase kit (US Biochemical Corporation, Cleveland, Ohio).

Cloning of U7.6 sFv Construct into PHEN 1

U7.6 sFv was cloned into PHEN 1, a bacterial expression vector that uses the pelB leader sequence to direct secretion of proteins into the periplasmic space (Marks, J. D., et al., *J. Mol. Biol.* 222: 581–597 (1991)). In order to test the feasibility of using the gene splicing by overlap extension method to make sFv, we remade the construct using four primers to amplify the U7.6 V regions. The two "outer" primers (U7.6 L5' Sfi and U7.6 H3' Not) contained appropriate restriction sites for insertion into the pHEN 1 expression vector. The "overlap" primers (U7.6 L3' link and U7.6 H5' link) contained sequences that were derived from the linker peptide. These were designed to be complementary to each other to allow subsequent annealing of the amplified V regions. In addition, as the Taq enzyme has 3' terminal adenylation activity, the inner primers were designed so that there would be a T residue complementary to the terminal A carried by the majority of the PCR products. These primers were used to amplify the V regions, using pBluescript U7.6 as a template, and then 0.1–1 ul of the product mixed together and reamplified using only the outer primers. The resulting PCR product, containing the entire sFv construct, was phenol and chloroform extracted and ethanol precipitated prior to being cut by SfiI and NotI restriction enzymes.

The cut product was electrophoresed through a 2% agarose gel, purified with Geneclean, and ligated into PHEN 1. The vector, designated pHEN-U7.6, was then electroporated into TG1 *E. coli* which were grown on 2×TY plates containing 50 µg/ml ampicillin and 1% glucose.

Production of sFv Protein

For production of the sFv protein ($V_L$-linker-$V_H$) it is necessary to transfer the plasmid into the HB2151 strain of *E. coli*. The phage origin of replication in pHEN 1 was used to make phage containing single stranded DNA derived from the PHEN 1 U7.6 plasmid. TG1 cells, carrying PHEN 1 U7.6 were grown in 2×TY medium containing ampicillin and glucose. They were infected with the VCS M13 helper phage (Stratagene) and grown overnight in 2×TY medium containing ampicillin, kanamycin and glucose. The phage were then precipitated from the supernatant with ⅕ volume of 20% polyethylene glycol 6000 and 2.5M NaCl and used to infect HB2151 cells, which were grown on 2×TY plates+ampicillin+glucose. Colonies capable of producing proteins were identified by induction of small cultures with IPTG, running the cell pellet on SDS-PAGE and identifying the protein by probing a Western blot with the anti-myc peptide antibody, as described below.

Western Blotting

Proteins were separated by SDS-PAGE on 12.5% gels using the Phastgel system (Pharmacia LKB, Piscataway, N.J.) as described by the manufacturers. The proteins were blotted onto nitrocellulose using the Phastgel Western blotting apparatus. The blots were then blocked in PBS containing 1% BSA for 30 min at room temperature, washed 5 times in PBS-tween and incubated for 1 hr at room temperature with PBS-Tween containing 2–7 µg/ml of the anti-peptide antibody (Mycl 9E10.2). After 5 more washes with PBS-Tween the blots were incubated for a further 30–60 min with 0.2 µg/ml of alkaline phosphatase conjugated goat anti-mouse IgG (Southern Biotechnology Associates), before 5 final washes with PBS-Tween. The blots were developed with 0.5 mg/ml nitroblue tetrazolium and 0.25 mg/ml 5-bromo-4-chloro-3-indolyl phosphate (Sigma) in 0.1M M NaHCO3 1 mM MgCl2 pH 9.8.

Induction and Production of sFv in pHEN U7.6

HB2151 cells containing pHEN1 U7.6 were grown in 2×TY medium containing ampicillin and glucose. When in mid-log phase the cells were spun, washed in LB broth, and resuspended in 2×TY medium containing ampicillin and 1 mM IPTG. The cells were then incubated, with shaking, at room temperature overnight, under conditions found in the initial studies, as described above, which produce the highest yield of cells. The cells were pelleted and stored at −20° C., and the supernatant filtered through a 0.45 μm filter.

Preparation of U7.6 sFv from Cell Pellet

The cell pellet was thawed and resuspended in cold 50 mM Tris, 1 mM EDTA, 100 mM KCl, 0.1 mM pH8.0, and disrupted with a Bead Beater (Biospec Products, Bartlesville, Okla.). 0.1 mm diameter glass beads were added and the cells pulsed 3×1 minute, with one minute cooling periods. Following lysis, the sFv protein was found in the insoluble fraction. Following spinning, this was taken up in 7.5M guanidine-HCl and the solution clarified by centrifugation at 25000 g for 20 min. The material was then dialyzed at 40° C. against 0.1M Tris, 2 mM EDTA, 0.4M arginine pH 8.0, and the active sFv recovered by affinity chromatography.

Figure 1:
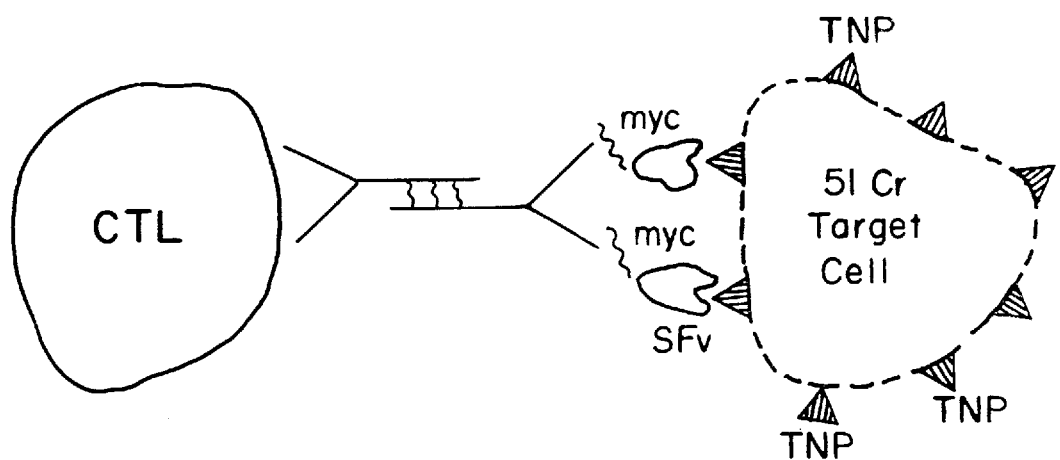
FIG. 1 is a schematic representation of a method of immunotherapy using monospecific binding proteins and multivalent antibodies.
Figure 2:
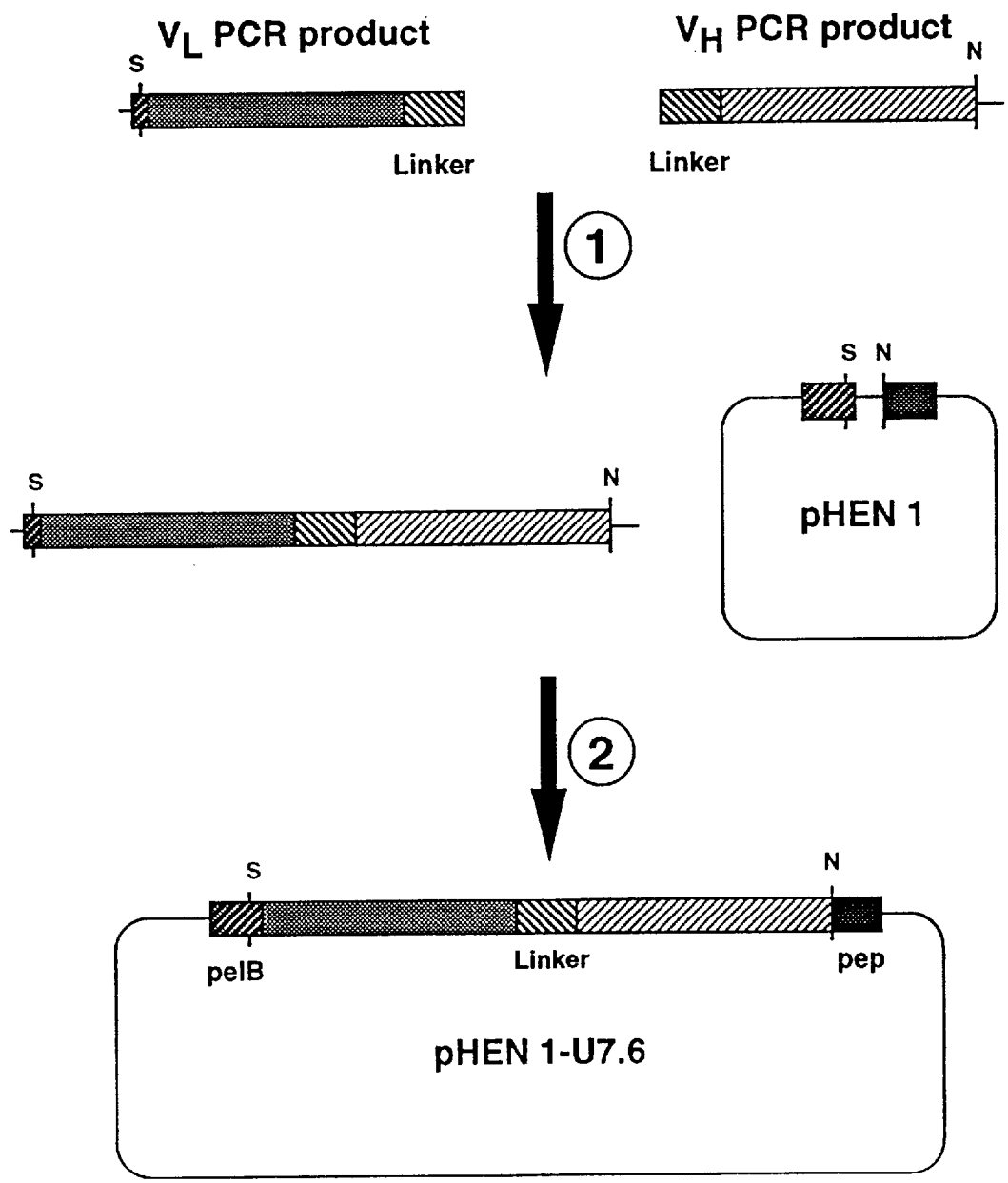
FIG. 2 is a schematic representation of the method of production of the U7.6 sFv. Step (1) shows the joining of VH and VL PCR products to yield the U7.6 sFv gene and Step (2) shows the combination of U7.6 sFv gene and the pHEN1 expression vector to yield the pHEN1-U7.6 plasmid.
Figure 4A:
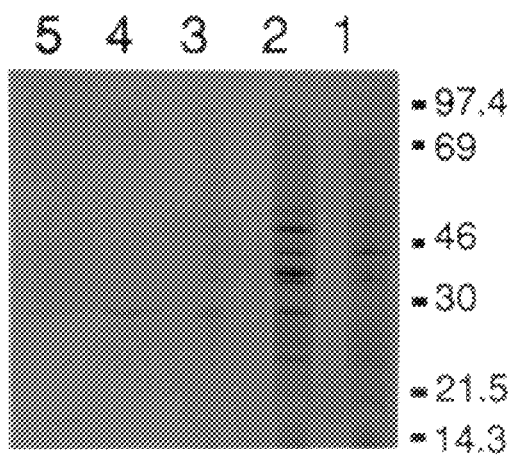
FIGS. 4A and 4B represent the results of SDS polyacrylamide gel electrophoresis (SDS-PAGE) and Western Blots of the U7.6 sFv during production and purification.
Figure 4B:
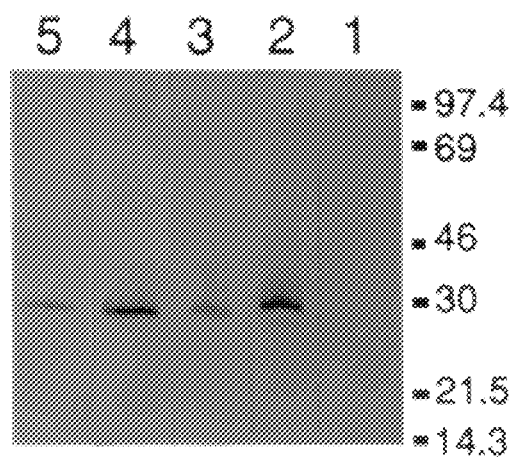

FIG. 4 represents the results of SDS polyacrylamide gel electrophoresis (SDS-PAGE) of the U7.6 sFv during production and purification. Samples were prepared for SDS-PAGE under reducing conditions and run on a 12.5% gel. The gels were stained with either Coomassie Blue or blotted onto nitrocellulose and probed with the anti-myc peptide antibody. Lane 1 is uninduced cell pellet; Lane 2 is induced cell pellet; Lane 3 is material after solubilization and dialysis against arginine; Lane 4 is U7.6 affinity purified from refolded material; Lane 5 is U7.6 sFv affinity purified from culture supernatant.

Size Separation and Affinity Purification of Active U7.6 sFv

Refolded sFv material was passed down a 1.6×50 cm Superdex 75 column (Pharmacia) using a Pharmacia FPLC system in 0.1M Tris, 2 mM EDTA, 0.4M arginine pH8.0, at a flow rate of 2 ml/minute.

The elution profile on refolded sFv and elution volumes of three calibrating proteins, cytochrome C (13 kD), human carbonic anhydrase (29.5 kD), and bovine serum albumen (67 kD) are shown in FIG. 5. Four ml. fractions were collected, and activity was determined by incubating 750 μl samples with DNP-Sepharose beads, in the presence or absence of 1 mM DNP hapten. The beads were pelleted and 1 μl samples of the supernatant dot blotted onto nitrocellulose, and assayed for the presence of U7.6 sFv using Mycl 9E10.2 antibody. The lower portion of FIG. 5 shows the results of dot blots of fractions assayed without adsorption (lane A), after adsorption with DNP-Sepharose beads (row B) or after adsorption with DNP-Sepharose beads in the presence of 1 mM DNP hapten (row C). The relative intensity of the dot blots is indicated by the symbol in each box (+++, intense; ++, strong; +, weak; +/−, borderline; blank, negative).

As shown in FIG. 5, the DNP Sepharose beads selectively removed the monomeric protein (lane B). This removal was blocked by 1 mM DNP hapten (lane C) showing that it was specific. The vast majority of active U7.6 sFv that binds to DNP-Sepharose therefore resides in the monomeric peak and most, if not all, of the monomeric protein is active. Thus, size exclusion chromatography provides a relatively simple method of separating active monomeric sFv from inactive sFv.

U7.6 sFv was also isolated by affinity chromatography using DNP-lysine- Sepharose. The sFv was eluted with 1 mM DNP ε-amino caproic acid, and the free hapten subsequently removed by dialysis against a suitable buffer containing Dowex AG 1-X8 beads (BioRad, Richmond, Calif.).

When affinity purified sFv was applied to a Superdex 75 column, it eluted at a volume slightly greater than that predicted by the sizing standards, suggesting that the protein is folded into a compact form but may be exhibiting a slight tendency for self-association. However, prior to affinity purification, most of the refolded U7.6 sFv eluted at the exclusion volume, as demonstrated by dot blotting the various fractions off the column and probing with anti-myc peptide antibody (FIG. 5, described above), which is consistent with a considerable degree of aggregate forming under the refolding conditions of this experiment, which masks the active monomeric sFv that is present.

Example 2

Cloning of OKT9 sFv in PHEN 1

The OKT9 sFv construct consists of the VL and VH domains linked by the same ((Gly)4Ser)3 linker used in the U7.6 sFv. The OKT9 sFv construct was PCR amplified using OKT9 5'SFI and OKT9 3'his NOT oligonucleotide primers, containing the SfiI and NotI restriction sites needed for cloning into PHEN 1. In addition, the OKT9 3'his NOT primer contained a sequence coding for six histidines. The PCR product was cut with the appropriate enzymes and ligated into PHEN 1 as described for U7.6 sFv.

Expression and Purification of OKT9 sFv

The OKT9 sFv was expressed in the same manner as U7.6 sFv. The induced cell pellet was lysed and the insoluble material dissolved in 6M guanidine, 0.1M $NaH_2PO_4$, 10 mM Tris, pH8.0. This was then mixed with $Ni^{2+}$-NTA-agarose beads (Quiagen, Chatsworth, Calif.), which bind the His6 tail, for 2 hrs at 4° C. The beads were extensively washed with the 6M guanidine-HCl buffer and the sFv material eluted with 100 mM imidazole. The sFv was allowed to renature by dialysis against 0.1M Tris, 2 mM EDTA, 0.4M arginine pH 8.0 and passed down a Superdex 75 column as described for the U7.6 sFv. Material that eluted as the monomeric sFv was then assayed for the presence of active OKT9 sFv.

Example 3

Surface Binding of sFv

The binding of U7.6 and OKT9 sFv to cells was tested by flow cytometry using TNP modified B6MC1 cells and K562 cells which express the human transferrin receptor recognized by OKT9. Cells were incubated with the sFv, washed, and stained with FITC labelled Mycl 9E10.2 (anti-tag peptide) antibody before analysis with a FACScan flow cytometer (Becton Dickinson, Mountain View, Calif.) with C30 software. Cells were gated for viability on both forward and side light scatter, and the fluorescence measured at 488 nm. In the case of U7.6 specificity was demonstrated by using DNP hapten, or U7.6 Fab, to inhibit the binding of the sFv.

FIG. 6, Panel B shows the binding of U7.6 sFv to TNP-coated MC-1 cells. The dotted line refers to cells stained with FITC-anti-peptide antibody alone; the solid line refers to cells preincubated with 125 nM U7.6 sFv and then stained with the FITC anti-peptide. By comparison, panel A shows cells stained with a FITC anti-mouse IgG alone (dotted line), or with U7.6 Fab, followed by the FITC-anti-mouse IgG. Panel C shows that the U7.6 sFv does not bind to MC-1 cells that were not labeled with TNP. (Dotted and solid lines are as in panel B). Panel D shows that both U7.6 sFv and Fab inhibit the binding of FITC-U7.6 intact IgG antibody to TNP-MC-1 cells. Sparsely spaced dots and solid lines represent unstained and stained TNP-MC-1 cells respectively. Dashes represent staining of TNP-MC-1 cells by the FITC-U7.6 in the presence of 130 nM U7.6 Fab, and closely spaced dots are in the presence of 125 nM U7.6 sFv.

FIG. 7 shows the relative binding of U7.6 sFv and Fab to TNP coated B6MC1 cells. TNP modified cells were incubated with different concentrations of either U7.6 sFv or U7.6 Fab (closed squares), followed by either FITC Mycl 9E10.2 antibody or FITC-goat anti-mouse antibody (closed triangles). The cells were then analyzed by FACS and the mean fluorescence intensity (MFI) of the cell populations calculated.

FIG. 8 shows the inhibition of U7.6 Fab binding to TNP modified B6MC1 cells by DNP-amino caproic acid. TNP modified B6MC1 cells were incubated with U7.6 sFv (filled triangles) or U7.6 Fab (filled squares) in the presence of varying concentrations of DNP hapten. The cells were stained with FITC-labeled second antibody and the mean fluorescence intensity (MFI) of each cell population was determined by FACS analysis.

FIG. 9 shows the inhibition of U7.6 Fab binding to TNP modified cells by U7.6 sFv. TNP modified B6MC1 cells were incubated with 125 nM, 41.7 nM or 13.9 nM U7.6 Fab in the presence of varying concentrations of U7.6 sFv. The cells were stained with FITC goat anti-mouse IgG, and the mean fluorescence intensity (MFI) determined by FACS analysis. The background MFI in the absence of any U7.6 Fab was 40.

FIG. 10 shows the binding of OKT9 sFv to K562 cells. The sparse dots refer to K562 cells stained with FITC-anti-peptide; the solid line refers to OKT9-sFv plus FITC-anti-peptide. The dense dots refer to OKT9-sFv plus FITC-anti-peptide, but inhibited with excess OKT9 antibody.

Example 4

Retargeting Experiments

Trinitrophenol (TNP)-modified B6MC1 cells or unmodified cells were used in a standard $^{51}$Cr release assay, together with human cytotoxic T cells as effectors, to demonstrate the ability of the U7.6 sFv to retarget lysis. Human peripheral blood T cells were coated with bispecific heteroconjugate antibody (0.31 g/ml anti-CD3×anti-tag peptide or 0.8 µg/ml anti-CD3×anti-DNP) prepared as described in Perez, P., et al., *Nature* 316: 354–356 (1985). Target cells (either TNP modified or unmodified B6MC1 cells, transferrin receptor transfected L cells, or HUT 102 cells) were labelled with $^{51}$Cr and used as target cells. The cells (1×10$^6$/ml) were incubated with either U7.6 or OKT9 sFv for 30 min at 4° C. 10$^{-4}$ target cells were then added to wells of a microtiter plate containing appropriate numbers of effector cells and, in some cases, free DNP hapten at a final concentration of 2.5×10$^{-4}$M. The plates were then incubated for 3–4 hrs at 37° C. in 5% $CO_2$, and the specific lysis determined as described in Perez, P., et al., *Nature* 316: 354–356 (1985); Segal, D. M., In: *Fc Receptors and the Action of Antibodies*, H. Metzger (ed.) American Society for Microbiology, Washington, D.C. pp. 291–301 (1990)).

Figure 11A:
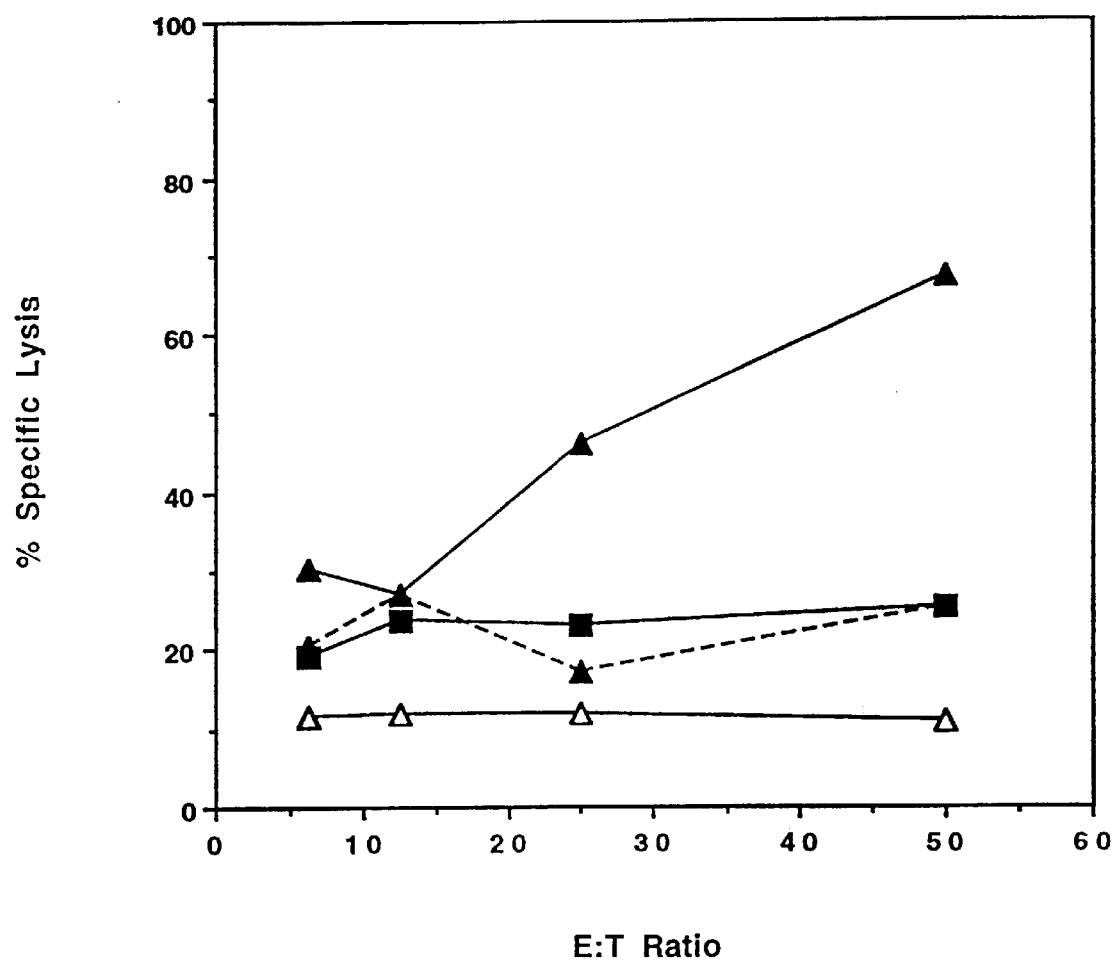
FIGS. 11A–C show the results of targeting of lysis using U7.6 sFv.
Figure 11B:
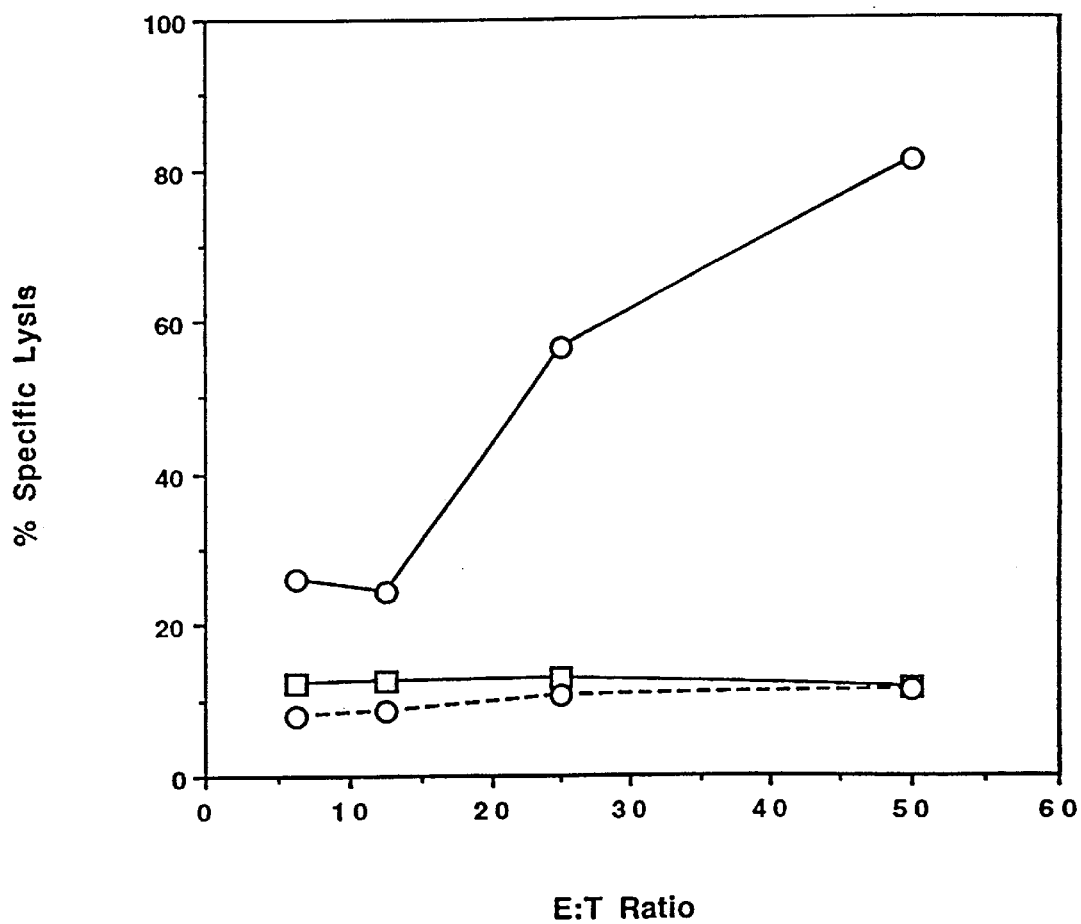
Figure 11C:
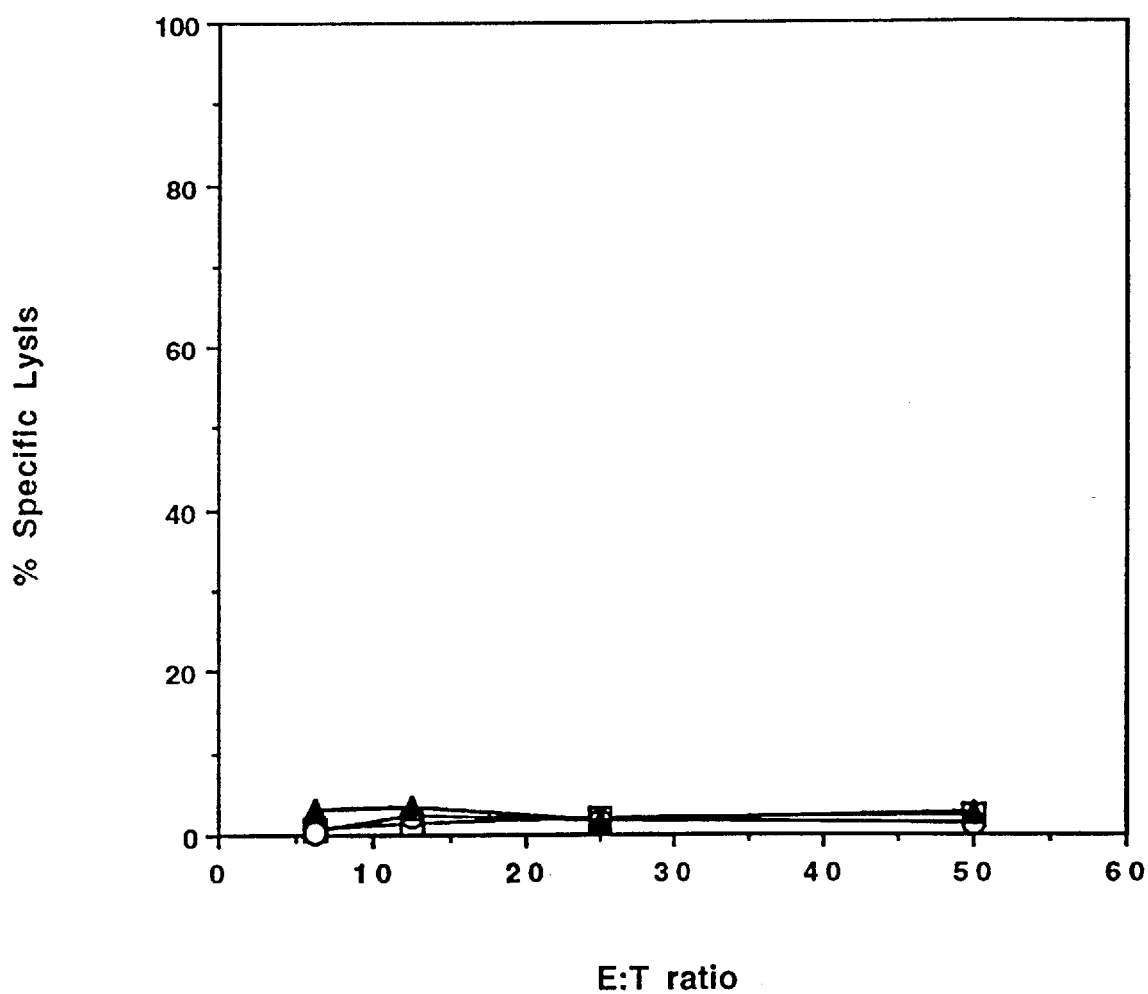

As shown in FIG. 11 panel A, significant lysis occurred when both U7.6 sFv and bispecific antibody (anti-CD3×anti-myc) were present (filled triangle, solid lines), much less lysis was seen in controls containing bispecific antibody alone (open triangles), U7.6 sFv alone (filled squares) or U7.6 sFv, bispecific antibody plus 1 mM DNP hapten (filled triangles, dashed lines). As a positive control (panel B), TNP-target cells were lysed by human T cells in the presence of anti-CD3×anti-DNP bispecific antibody (open circles), but not in the presence of no antibody (open triangles) or when 1 mM DNP-hapten was present (open circles, dashed lines). Finally no lysis was observed when target cells were not coated with TNP (Panel C), with either no antibody (open squares), anti-CD3×anti-DNP (open circles) or anti-CD3×anti-myc (filled triangles).

FIG. 12 shows the data resulting from lysis of TNP-TFR-transfected L cells by activated human T cells. The filled circles dashed lines, refer to effector cells and target cell with no antibody. The filled triangles refer to cells plus anti-CD3×anti-peptide bispecific antibody. The open squares refer to OKT9-sFv plus cells and bispecific antibody. The filled circles, solid lines refer to U7.6-sFv plus cells and bispecific antibody. The X axis represents the effector cell: target cell ratio. The Y axis represents the percent specific lysis as measured by $^{51}$Cr release.

Equivalents

Those skilled in the art will recognize, or be able to ascertain using no more than routine experimentation, many equivalents to the specific embodiments of the invention described herein. Such equivalents are intended to be encompassed by the following claims.

---

We claim:

1. A method for delivering an agent to target cells comprising the steps of:
   a) providing a single-chain antibody-peptide tag fusion protein, or a single-chain T-cell receptor-peptide tag fusion protein, wherein the single-chain antibody, or T-cell receptor is specific for one, or more, naturally-occurring cell surface markers on the target cells and the peptide tag comprises an amino acid sequence of about 11 to 17 amino acid residues;

b) contacting the target cells with the single-chain antibody, or single-chain T-cell receptor fusion protein, under conditions whereby the single-chain antibody or T-cell receptor binds to the cell surface markers of the target cells, thereby producing peptide-tagged target cells;

c) providing a bispecific antibody having two binding sites, wherein one binding site is specific for the peptide tag and the other binding site is specific for the agent to be delivered; and d) contacting the bispecific antibody with the peptide-tagged target cells and the agent to be delivered, under conditions whereby the bispecific antibody binds to the peptide tag on the target cells and to the agent, thereby delivering the agent to the target cells.

2. The method of claim 1 wherein the peptide tag comprises the amino acid sequence SEQ ID NO:5.

3. The method of claim 1 wherein the bispecific antibody is a crosslinked antibody fragment.

4. The method of claim 3 wherein the antibody fragment is an Fab.

5. A method for delivering a cytotoxic agent to target cells in a host comprising the steps of:

a) administering to the host a single-chain antibody-peptide tag fusion protein, wherein the single-chain antibody is specific for one, or more, naturally-occurring cell surface markers on the target cells and the peptide tag comprises an amino acid sequence of about 11 to 17 amino acid residues, under conditions whereby the single-chain antibody-peptide fusion protein binds to the cell surface markers of the target cells, thereby producing peptide-tagged target cells; and b) administering to the host a bispecific antibody having two binding sites, wherein one binding site is specific for the peptide tag and the other binding site is specific for the cytotoxic agent to be delivered, under conditions whereby the bispecific antibody binds to the peptide tag on the target cells and to the cytotoxic agent, thereby delivering the cytotoxic agent to the target cells.

6. The method of claim 5 wherein the peptide tag comprises the amino acid sequence SEQ ID NO:5.

7. The method of claim 5 wherein the cytotoxic agent is a cytotoxic T-lymphocyte.

8. The method of claim 7 wherein one binding site of the bispecific antibody is reactive with the cell surface marker, CD3.

9. The method of claim 5 wherein the single-chain antibody-peptide tag fusion proteins comprise a mixture of single-chain antibody-peptide tag fusion proteins wherein each single-chain antibody is specific for a different cell surface marker or the target cells.

10. A method for delivering a cytotoxic agent to target cells in a host comprising the steps of:

a) administering to the host a single-chain T-cell receptor-peptide tag fusion protein, wherein the single-chain T-cell receptor is specific for one, or more, naturally-occurring cell surface markers on the target cells and the peptide tag comprises an amino acid sequence of about 11 to 17 amino acid residues, under conditions whereby the single-chain T-cell receptor-peptide fusion protein binds to the cell surface markers of the target cells, thereby producing peptide-tagged target cells; and b) administering to the host a bispecific antibody having two binding sites, wherein one binding site is specific for the peptide tag and the other binding site is specific for the cytotoxic agent to be delivered, under conditions whereby the bispecific antibody binds to the peptide tag on the target cells and to the cytotoxic agent thereby delivering the cytotoxic agent to the target cells.

11. The method of claim 10 wherein the peptide tag comprises the amino acid sequence SEQ ID NO:5.

12. The method of claim 10 wherein the cytotoxic agent is a cytotoxic T-lymphocyte.

13. The method of claim 12 wherein one binding site of the bispecific antibody is reactive with the cell surface marker, CD3.

14. A method of immunotherapy in a host comprising the steps of:

a) administering to the host a single-chain antibody-peptide tag fusion protein, wherein the single-chain antibody is specific for one, or more, naturally-occurring cell surface markers on the target cells and the peptide tag comprises an amino acid sequence of about 11 to 17 amino acid residues, under conditions whereby the single-chain antibody-peptide fusion protein binds to the cell surface markers of the target cells, thereby producing peptide-tagged target cells; and b) administering to the host a bispecific antibody having two binding sites, wherein one binding site is specific for the peptide tag and the other binding site is specific for an agent to be delivered, under conditions whereby the bispecific antibody binds to the peptide tag on the target cells and to the agent, thereby delivering the agent to the target cells.

15. The method of claim 14 wherein the peptide tag comprises the amino acid sequence SEQ ID NO:5.

16. The method of claim 14 wherein the single-chain antibody-peptide tag fusion proteins comprise a mixture of single-chain antibody-peptide tag fusion proteins wherein each single-chain antibody is specific for a different cell surface marker or the target cells.

17. A method for imaging specific tissue in a host comprising the steps of:

a) administering to the host a single-chain antibody-peptide tag fusion protein, or a single-chain T-cell receptor-peptide tag fusion protein, wherein the single-chain antibody or single-chain T-cell receptor, is specific for one, or more, naturally-occurring cell surface markers on the target cells and the peptide tag comprises an amino acid sequence of about 11 to 17 amino acid residues, under conditions whereby the single-chain antibody, or T-cell receptor binds to the cell surface markers of the target cells, thereby producing peptide-tagged target cells; and b) administering to the host a bispecific antibody having two binding sites, wherein one binding site is specific for the peptide tag and the other binding site is specific for an imaging agent to be delivered, under conditions whereby the bispecific antibody binds to the tag on the target cells and to the imaging agent, thereby delivering the imaging agent to the target cells.

18. The method of claim 17 wherein the peptide tag comprises the amino acid sequence SEQ ID NO:5.

19. A method for delivering an agent to target cells in a host comprising the steps of:

a) administering to the host a single-chain antibody-peptide tag fusion protein, or a single-chain T-cell receptor-peptide tag fusion protein, wherein the single-chain antibody, or T-cell receptor, is specific for one, or more, naturally-occurring cell surface markers on the target cells and the peptide tag comprises an amino acid sequence of about 11–17 amino acid residues, under conditions whereby the single-chain antibody, or T-cell receptor binds to the cell surface markers of the target cells, thereby producing peptide-tagged target cells;

b) providing a bispecific antibody having two binding sites, wherein one binding site is specific for the peptide tag and the other binding site is specific for the agent to be delivered; and c) contacting, in vitro, said bispecific antibody with the agent to be delivered under conditions whereby the agent binds to the bispecific antibody, thereby producing an agent-bound bispecific antibody; and d) administering the agent-bound bispecific antibody to the host under conditions whereby the bispecific antibody binds to the peptide-tagged target cell, thereby delivering the agent to the target cell.

20. The method of claim 19 wherein the peptide tag comprises the amino acid sequence SEQ ID NO.:5.

21. The method of claim 19 wherein the cytotoxic agent is a cytotoxic T-lymphocyte.

22. A method of redirecting cytotoxic T-lymphocytes to target cells comprising the steps of:

a) providing a single-chain antibody-peptide tag fusion protein, or single-chain T-cell receptor-peptide tag fusion protein, wherein the single-chain antibody or T-cell receptor is specific for one, or more, naturally-occurring cell surface markers on the target cells and the peptide tag comprises SEQ ID NO. 5;

b) contacting the target cells with the single-chain antibody, or T-cell receptor, fusion protein under conditions whereby the single-chain antibody or T-cell receptor binds to the cell surface markers of the target cells, thereby producing peptide-tagged target cells;

c) providing a bispecific antibody having two binding sites, wherein one binding site is specific for SEQ ID NO. 5 and the other binding site is specific for the cytotoxic T-lymphocyte; and d) contacting the peptide-tagged target cells with the bispecific antibody, under conditions whereby the bispecific antibody binds to SEQ ID NO:5, thereby binding to the target cells, and the cytotoxic T-lymphocyte binds to the bispecific antibody, thereby redirecting the cytotoxic T-lymphocyte to the target cells.

* * * * *